(12) United States Patent
Schuetzle et al.

(10) Patent No.: US 11,498,886 B2
(45) Date of Patent: Nov. 15, 2022

(54) CATALYSTS AND PROCESSES FOR THE DIRECT PRODUCTION OF LIQUID FUELS FROM CARBON DIOXIDE AND HYDROGEN

(71) Applicant: CARBON RECYCLING SOLUTIONS, LLC, Sacramento, CA (US)

(72) Inventors: Robert Schuetzle, Sacramento, CA (US); Dennis Schuetzle, Grass Valley, CA (US)

(73) Assignee: Infinium Technology, LLC, Sacramento, CA (US)

( * ) Notice: Subject to any disclaimer, the term of this patent is extended or adjusted under 35 U.S.C. 154(b) by 0 days.

(21) Appl. No.: 16/873,561

(22) Filed: May 4, 2020

(65) Prior Publication Data

US 2021/0340075 A1   Nov. 4, 2021

(51) Int. Cl.
   *C07C 1/04*   (2006.01)
   *B01J 23/00*  (2006.01)
   (Continued)

(52) U.S. Cl.
   CPC ............ *C07C 1/0435* (2013.01); *B01J 21/08* (2013.01); *B01J 23/005* (2013.01); *B01J 23/02* (2013.01);
   (Continued)

(58) Field of Classification Search
   CPC ......... C01B 32/50; C10G 2/32; C07C 1/0435; C07C 2523/755; B01J 21/08;
   (Continued)

(56) References Cited

U.S. PATENT DOCUMENTS

| 4,990,491 A | 2/1991 | Wagner et al. |
| 6,402,989 B1 | 6/2002 | Gaffney et al. |

(Continued)

FOREIGN PATENT DOCUMENTS

| AU | 2015/203898 B2 | 8/2015 |
| GB | 2279583 | 1/1995 |

OTHER PUBLICATIONS

Allam, R., et al., "High efficiency and low cost of electricity generation from fossil fuels while eliminating . . . " Energy Procedia 37, 1135-1149 (2013).

(Continued)

*Primary Examiner* — Jafar F Parsa
(74) *Attorney, Agent, or Firm* — McKinney Law Group APC; Jeffrey A. McKinney

(57) ABSTRACT

Embodiments of the present invention relates to two improved catalysts and associated processes that directly converts carbon dioxide and hydrogen to liquid fuels. The catalytic converter is comprised of two catalysts in series that are operated at the same pressures to directly produce synthetic liquid fuels or synthetic natural gas. The carbon conversion efficiency for $CO_2$ to liquid fuels is greater than 45%. The fuel is distilled into a premium diesel fuels (approximately 70 volume %) and naphtha (approximately 30 volume %) which are used directly as "drop-in" fuels without requiring any further processing. Any light hydrocarbons that are present with the carbon dioxide are also converted directly to fuels. This process is directly applicable to the conversion of $CO_2$ collected from ethanol plants, cement plants, power plants, biogas, carbon dioxide/hydrocarbon mixtures from secondary oil recovery, and other carbon dioxide/hydrocarbon streams. The catalyst system is durable, efficient and maintains a relatively constant level of (Continued)

fuel productivity over long periods of time without requiring re-activation or replacement.

11 Claims, 5 Drawing Sheets

(51) Int. Cl.
| | |
|---|---|
| B01J 23/02 | (2006.01) |
| B01J 37/02 | (2006.01) |
| B01J 35/10 | (2006.01) |
| B01J 21/08 | (2006.01) |
| B01J 23/83 | (2006.01) |
| B01J 23/89 | (2006.01) |
| B01J 23/889 | (2006.01) |
| C01B 32/50 | (2017.01) |
| C25B 1/04 | (2021.01) |
| B01J 23/755 | (2006.01) |

(52) U.S. Cl.
CPC ............. B01J 23/755 (2013.01); B01J 23/83 (2013.01); B01J 23/8896 (2013.01); B01J 23/892 (2013.01); B01J 35/1014 (2013.01); B01J 37/0225 (2013.01); B01J 37/0242 (2013.01); C01B 32/50 (2017.08); C25B 1/04 (2013.01); *C07C 2523/755* (2013.01); *F25J 2215/50* (2013.01)

(58) Field of Classification Search
CPC ........ B01J 23/005; B01J 23/755; B01J 23/83; B01J 23/02; C25B 1/04
See application file for complete search history.

(56) References Cited

U.S. PATENT DOCUMENTS

| | | | |
|---|---|---|---|
| 6,432,665 | B1 | 8/2002 | Okado et al. |
| 6,946,114 | B2 | 9/2005 | Allison et al. |
| 7,432,222 | B2 | 10/2008 | Choudhary et al. |
| 7,718,832 | B1 | 5/2010 | Schuetzle et al. |
| 8,198,338 | B2 | 6/2012 | Schulenberger et al. |
| 8,394,862 | B1 | 3/2013 | Schuetzle et al. |
| 8,741,001 | B1 | 6/2014 | Schuetzle et al. |
| 9,090,831 | B2 | 7/2015 | Schuetzle et al. |
| 9,095,813 | B2 | 8/2015 | Keith et al. |
| 9,476,002 | B1 | 10/2016 | Schuetzle et al. |
| 9,611,145 | B2 | 4/2017 | Schuetzle et al. |
| 9,631,147 | B2 | 4/2017 | Schuetzle et al. |
| 10,478,806 | B2 | 11/2019 | Schuetzle et al. |
| 2003/0113244 | A1 | 6/2003 | Dupont et al. |
| 2005/0166447 | A1 | 8/2005 | Corkwell et al. |
| 2006/0144755 | A1 | 7/2006 | Benazzi et al. |
| 2008/0108716 | A1 | 5/2008 | Ayasse |
| 2009/0300970 | A1 | 12/2009 | Perego et al. |
| 2010/0160463 | A1 | 6/2010 | Wang et al. |
| 2011/0044860 | A1* | 2/2011 | Severinsky ............... C10J 3/18 422/187 |
| 2012/0208902 | A1 | 8/2012 | Kresnyak et al. |
| 2016/0362611 | A1* | 12/2016 | Harris ................... C07C 29/151 |
| 2017/0321333 | A1 | 11/2017 | Kuhl et al. |

OTHER PUBLICATIONS

Allam, R., et al., "Demonstration of the Allam cycle: an update on the development status of a high efficiency supercritical carbon . . . " Energy Procedia 114, 5949-5966 (2017).

Arakawa, H., "Catalysis research of relevance to carbon management: progress, challenges, and opportunities" Chem. Rev. 101, 953-996 (2001).

Artz, J., et al., "Sustainable conversion of carbon dioxide: An integrated review of catalysis and life cycle assessment" Chemical Reviews, 118, 434-504 (2018).

Ashcroft, A.T., et al., "Partial oxidation of methane to synthesis gas using carbon dioxide" Nature, 352, 255-256 (1991).

Bahmanpour, A.M., et al., "Cu—Al spinel as a highly active and catalyst for the reverse water gas shift reaction" ACS Catal., 9, 6243-6251 (2019).

Centi, G., et al, "Opportunities and prospects in the chemical recycling of carbon dioxide to fuels" Catalysis Today 148, 191-205 (2009).

Fan, M., et al, "Catalytic technology for carbon dioxide reforming of methane to syngas" ChemCatChem 1, 192-208 (2009).

Choudhary, V.R., et al, "Energy efficient methane-to-syngas conversion with low H2/CO ratio by simultaneous catalytic reactions . . . " Catalysis Letters, 32, 391-396 (1995).

Daza, Y.A. et al., "CO2 conversion by reverse water gas shift catalysis: Comparison of catalysts, mechanisms . . . " Royal Society of Chemistry Advances, 1-31 (2016).

Hill, M.R., "How to make renewable natural gas" 2018 AGA-EPA RNG Workshop (Oct. 23, 2018).

Intergovernmental Panel on Climate Change: IPCC special report on CO2 capture and storage, Cambridge University Press, Cambridge (2005).

Jafari, M., et al, "Plant-wide simulation of an integrated zero-emission process to convert flare gas to gasoline" Gas Processing Journal, 6, 1-20 (2018).

Jiang, Z., et al, "Turning carbon dioxide into fuel" Phil. Trans. R. Soc. A, 368, 3343-3364 (2010).

Kothandaraman, J., et al., "Conversion of CO2 from air into methanol using a polyamine and a homogeneous ruthenium catalyst" J. Am. Chem. Soc. 138, 778-781 (2016).

Li, W., et al., "A short review of recent advances in CO2 hydrogenation to hydrocarbons over heterogeneous catalysts" RSC Adv., 8, 7651 (2018).

Lortie, M., "Reverse water gas shift reaction over supported Cu—Ni nanoparticle catalysts" Dept. of Chem. and Bio. Eng. M.S. Thesis, University of Ottawa, Canada (2014).

Marti, C., et al., "Simulation of methane production from carbon dioxide . . . " ICCSA 2016: Computational Science and Its Applications—ICCSA, 319-333 (2016).

Melaina, M.W., et al., "Blending hydrogen into natural gas pipeline networks: a review of key issues" National Renewable Energy Laboratory, Technical Report #5600-51995 (2013).

Messias, S., et al., "Electro-chemical production of syngas from CO2 at pressures up to 30 bars in electrolytes containing ionic liquid" React. Chem. Eng., 4, 1982-1990 (2019).

Mikkelsen, M., et al., "The teraton challenge—a review of fixation and transformation of carbon dioxide" Energy Environ. Sci. 3, 43-81 (2010).

National Academy of Sciences, "Chemical Utilization of CO2 into Chemicals and Fuels, Gaseous Carbon Waste Streams Utilization" Nat'l Academies Press, Washington D.C. (2019).

Olah, G. A., et al., "Chemical recycling of carbon dioxide to methanol and dimethyl ether—from greenhouse gas to renewable, . . . " J. Org. Chem. 74, 487-498 (2009).

Owen, R. E., et al, "Kinetics of CO2 hydrogenation to hydrocarbons over Iron-Silica catalysts" Physical Chemistry, 18, 3211-3218 (2017).

Pan, X., et al, "Enhanced ethanol production inside carbon-nanotube reactors containing catalytic particles" Nat. Mater. 6, 507-511 (2007).

Ruckenstein, E., et al, "Combination of CO2 reforming and partial oxidation of methane over NiO/MgO Solid Solution" Industrial & Eng. Chem. Res., 37, 1744-1747 (1998).

Sakakura, T., et al, "Transformation of carbon dioxide" Chem. Rev. 107, 2365-2387 (2007).

Safriet, D., "Emission factor documentation for AP-12, Section 9.12.2 Wines and Brandy" U.S. EPA, Office of Air Quality, Research Triangle Park, NC (Oct. 1995).

Semelsberger, T.A., et al., "Dimethyl Ether (DME) as an alternative fuel" Journal of Power Sources 156, 497-511 (2006).

SoCalGas, "Renewable natural gas (RNG) gas quality standards" (www.socalgas.com/rg) (2017).

Schuetzle, D., et al., "Solar reforming of carbon dioxide to produce diesel fuel" DOE report #DE-FE0002558 (2010).

(56) References Cited

OTHER PUBLICATIONS

Schuetzle, D., "Historical and predicted global climate changes . . . " 2018 Global Climate Action Summit, San Francisco, CA, www.researchgate.net (Apr. 24, 2017 & Jan. 26, 2020 update).
Vogt, C., et al, "The renaissance of the Sabatier reaction and its applications on Earth and in space" Nature Catalysis, 2, 188-197 (2019).
Wang, W., et al, "Recent advances in catalytic hydrogenation of carbon dioxide" Chem. Soc. Rev, 40, 3703-3727 (2011).
Wang, Y., et al, "High temperature solid oxide H2O/CO2 co-electrolysis for syngas production" Fuel Processing Technology, 161 (2016).
Williamson, D., et al, "N-doped Fe for combined RWGS-FT CO2 hydrogenation" 7, 7395-7402, ACS Sustainable Chem. Engineering (2019).
Wieclaw-Solny, L., et al, "The technological research progress of amine-based CO2 capture" Polityka Energ. 16, 229-240 (2013).
Wikipedia: Energy density (2022) (www.en.wikipedia.org/wiki-/Energy_density).
Zaki, T., et al, "Natural gas origin, composition and processing: a review" Journal of Natural Gas Science and Engineering 34 (2016).
Zhang, J., et al, "Development of stable bimetallic catalysts for carbon dioxide reforming of methane" Journal of Catalysis, 249, 300-310 (2007).
Zhu, Q., "Developments on CO2-utilization technologies" Clean Energy, 3, 85-100 (2019).

\* cited by examiner

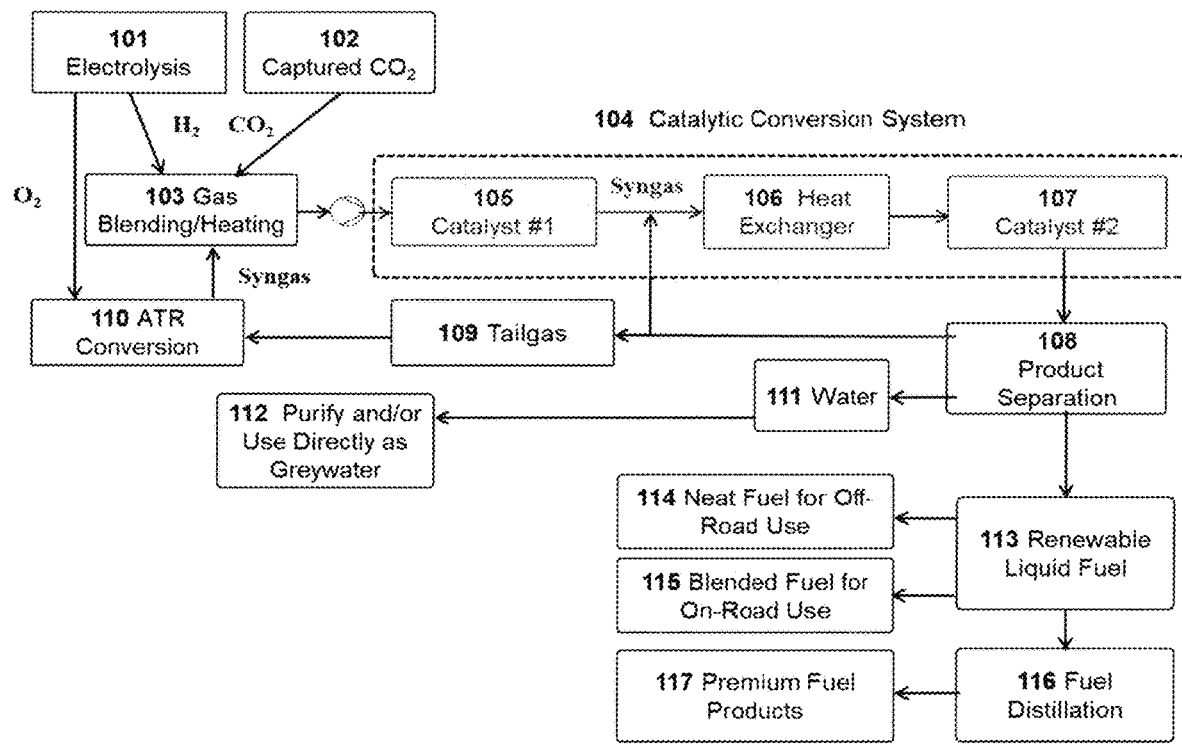
FIG. 1 – Integrated Catalytic Converter and Process for the Production of Renewable Liquid fuels

FIG. 2 – Potential Reactions and Side Reactions for the Catalytic Conversion of $CO_2$ and $H_2$ to CO

| |
|---|
| 201. $CO_2$ Hydrogenation ($CO_2 + H_2 = CO + H_2O$) ($\Delta H_{298} = +42.1$ kJ/mole) |
| 202. $CO_2$ Hydrogenation ($CO_2 + 4H_2 = CH_4 + 2H_2O$) ($\Delta H_{298} = -165.0$ kJ/mole) |
| 203. $CH_4$ Dry Reforming ($CO_2 + CH_4 = 2CO + 2H_2$) ($\Delta H_{298} = +247.0$ kJ/mole) |
| 204. $C_2H_6$ Dry Reforming ($2CO_2 + C_2H_6 = 4CO + 3H_2O$) ($\Delta H_{298} = +134.0$ kJ/mole) |
| 205. CO Hydrogenation ($CO + 2H_2 = CH_4 + H_2O$) ($\Delta H_{298} = -206.1$ kJ/mole) |
| 206. $CH_4$ Steam Reforming ($CH_4 + H_2O = CO + 3H_2$) ($\Delta H_{298} = +206.1$ kJ/mole) |
| 207. $C_2H_6$ Steam Reforming ($C_2H_6 + 2H_2O = 2CO + 5H_2$) ($\Delta H_{298} = +136.0$ kJ/mole) |
| 208. Water Gas Shift ($CO + H_2O = H_2 + CO_2$) ($\Delta H_{298} = -41.2$ kJ/mole) |
| 209. $CO_2$ Reduction (coking) ($CO_2 + 2H_2 = C + 2H_2O$) ($\Delta H_{298} = -90.1$ kJ/mole) |
| 210. $CH_4$ Reduction (coking) ($CH_4 + H_2 = C + 3H_2$) ($\Delta H_{298} = -165.0$ kJ/mole) |
| 211. CO Reduction (coking) ($CO + H_2 = C + H_2O$) ($\Delta H_{298} = -131.3$ kJ/mole) |
| 212. CO Reduction (coking) ($2CO = C + CO_2$) ($\Delta H_{298} = -172.4$ kJ/mole) |
| 213. Methane Cracking ($CH_4 = 2H_2 + C$) ($\Delta H_{298} = +74.8$ kJ/mole) |

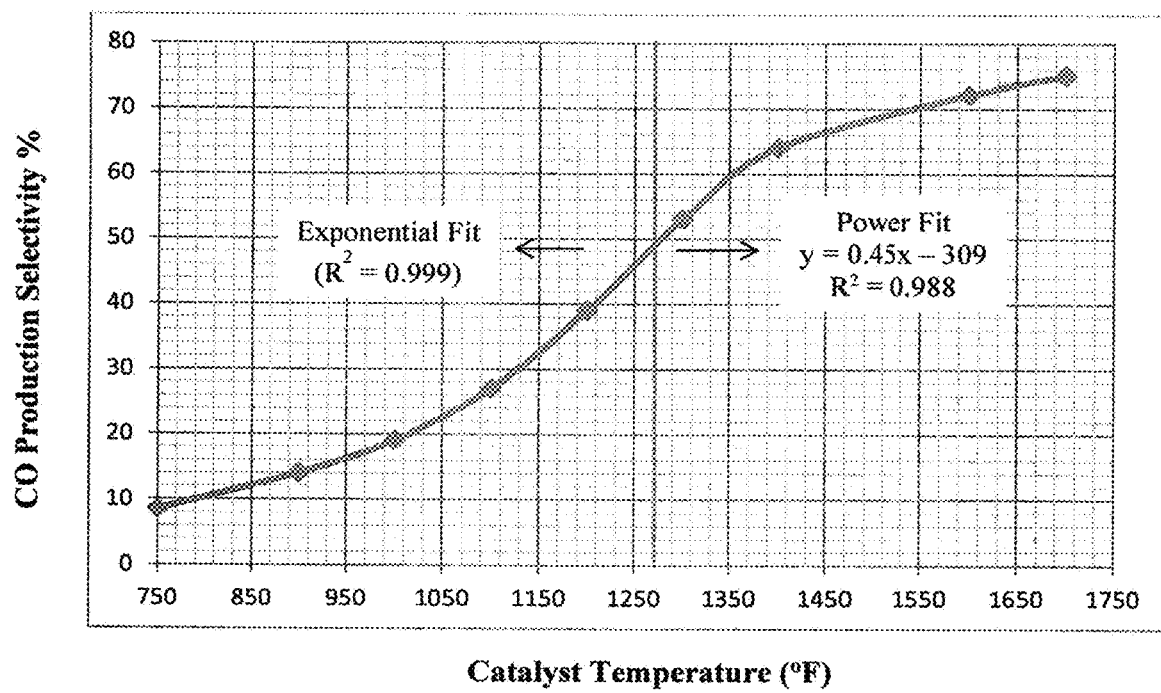
FIG. 3 – The Effect of Operating Temperature on the Production of CO at 50 psi by the $CO_2$ Reforming Catalyst

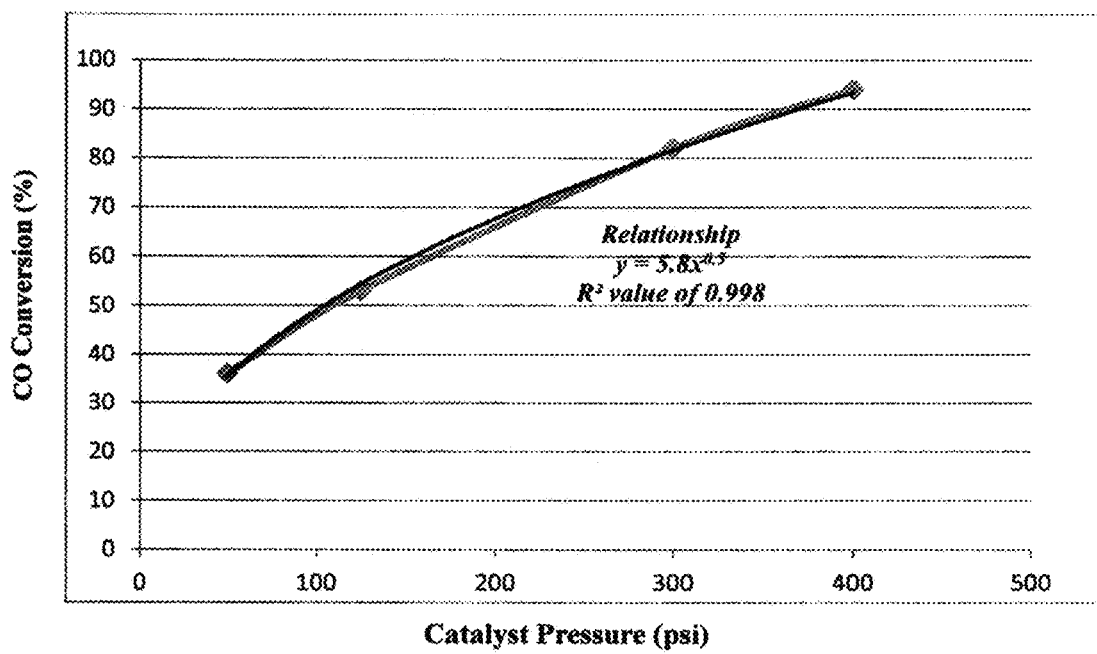
FIG. 4 – The Relationship between Catalyst #2 Operating Pressure on CO Conversion Efficiency at 450 °F

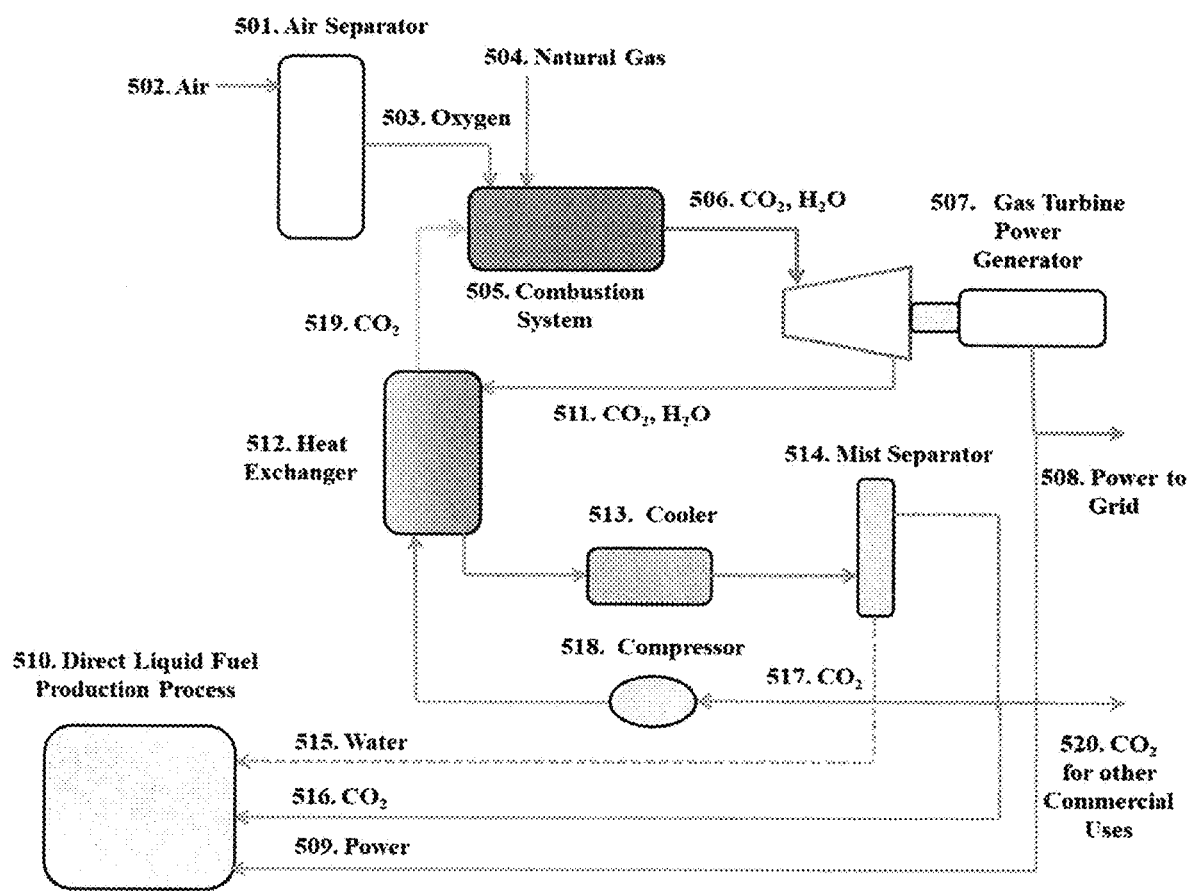
Figure 5 - Integration of the Direct Liquid Fuel Production Process with an Allam Oxy-Fuel Combustion Process

CATALYSTS AND PROCESSES FOR THE DIRECT PRODUCTION OF LIQUID FUELS FROM CARBON DIOXIDE AND HYDROGEN

FIELD OF THE INVENTION

The present invention relates to improved catalysts and processes that can efficiently and economically convert $CO_2$ and $H_2$ mixtures directly to liquid fuels in two main steps. The catalytic process employs two enhanced catalysts that function efficiently in series at similar pressures, simplifying the overall process of producing fuels from non-petroleum feedstocks. Catalyst #1 converts $H_2$ and $CO_2$ mixtures to syngas with an $H_2$ to CO ratio of about 1.5-2.5 and catalyst #2 produces synthetic liquid fuels (and other products) directly from the syngas. $H_2$ and 02 are produced from water using electrolysis. The tailgas ($C_1$-$C_5$ HC's, $H_2$, CO and $CO_2$) from the catalytic process is partially oxidized with $O_2$ to produce additional syngas and heat. This commercial-scale process is applicable to the conversion of $CO_2$ collected from fermentation processes; cement plants; power plants; ambient air $CO_2$ capture systems (Direct Air Capture); coal power plants, natural gas processing plants, natural gas power plants, ammonia facilities, chemical facilities, and other significant sources of $CO_2$ (IPCC, 2005; Schuetzle, et al, 2010; Wieclaw-Solny et al, 2013). Light hydrocarbons present in the $CO_2$ are also converted to syngas. The liquid fuels produced include premium kerosene, diesel and jet fuels, and gasoline blendstocks. The reduction in greenhouse gas emissions for the liquid fuels varies from about 50-130%, depending upon the $CO_2$ source and the source of the power used for $H_2$ production. In addition to reducing greenhouse gas emissions, the synthetic diesel fuel reduces criteria pollutant emissions and improves fuel economy. This simplified 2-step catalytic process is durable, efficient and maintains a relatively constant level of fuel productivity over long periods of time without requiring catalyst re-activation or replacement.

BACKGROUND OF THE INVENTION

This invention is primarily focused on improved catalysts and associated processes that efficiently and economically converts $CO_2$ and $H_2$ mixtures directly to liquid fuels that reduce greenhouse gas emissions. These liquid fuels are often referred to as low carbon liquid fuels (LCLF), zero carbon fuels, ultra-low carbon fuels, or green fuels.

There are several reasons why fossil fuels remain so popular (Fulkerson et al. 1990).
1. They are available in one form or another in virtually all regions globally since the infrastructure for gaseous and liquid fuels distribution is extensive.
2. They can be used effectively to provide energy for a myriad of applications at every scale.
3. They are without equal as fuels for transportation since they are portable and contain a considerable amount of stored chemical energy. Therefore, liquid fuels will continue to be the overwhelming energy source for transportation.

However, since the production and combustion of fossil fuels produce significant quantities of the greenhouse gases, $CO_2$ and $CH_4$, a global objective has been to replace fossil fuels with low carbon liquid fuels (LCLF) and/or low carbon natural gas (LCNG) (Schuetzle, 2018).

Although $CO_2$ can be converted to low carbon natural gas (LCNG) (Marti et al, 2016; Hill, 2018) there are several advantages to the conversion of $CO_2$ to LCLF instead of LCNG as follows:
1. The energy densities of diesel and gasoline fuels are about 38.6 and 34.2 MJ/liter, respectively. These energy densities are much higher than that of $CH_4$ (9.0 MJ/liter @ 250 bar); $H_2$ (5.3 MJ/liter @ 690 bar); dimethyl ether (21.2 MJ/liter @ 5 bar); methanol (15.6 MJ/liter); lithium-ion batteries (1.76 MJ/liter) and lead acid batteries (0.56 MJ/liter) (Wikipedia, 2019).
2. The production of $CH_4$ from $CO_2$ requires about four times as much $H_2$ as the production of liquid fuels from $CO_2$.
3. Diesel and gasoline fuels can be stored at or near atmospheric pressure compared to 200-400 bars for $CH_4$ and 340-690 bars for $H_2$.
4. The global distribution infrastructure of liquid fuels is extensive and they can be transported easily to nearly any location on the planet.
5. It is challenging to produce synthetic $CH_4$ that can meet natural gas pipeline standards (Zhou et al, 2010; Melaina et al, 2013; Zaki et al, 2016; SoCalGas, 2019).

As a result, there has been an increasing interest in the development of efficient and economical technologies for the conversion of $CO_2$ to liquid fuels (Arakawa et al, 2001; Olah et al, 2005; Sakakura et al, 2007; Centi et al, 2009; Olah et al, 2009; Mikkelsen et al, 2010; Artz et al, 2018; Li et al, 2018).

This improved catalyst and process offers the intriguing possibility of using primary energy from renewable, carbon-free sources (such as electricity derived from solar, wind, wave/tidal, hydro or nuclear) to convert $CO_2$, in association with hydrogen into high-density vehicle fuels that are compatible with our current transportation infrastructure. In addition, this next-generation technology will help the expansion of more efficient power plants that produce little or no emissions such as oxy-combustion plants. Oxy-combustion plants refer to power plants that produce power from natural gas and oxygen, whose effluent is a nearly pure $CO_2$ stream (instead of a diluted $CO_2$ stream as is produced from traditional power plants).

Its real attraction is that this approach offers the prospect of significantly reducing the carbon emissions from transportation systems without the paradigm shift in infrastructure required by electrification of the vehicle fleet or by conversion to a hydrogen economy (Pearson et al. 2009).

Most of the prior art on the development of $CO_2$ to liquid fuels has focused on the production of gasoline and diesel fuels as "drop-in" fuels. Dimethyl ether (DME) is a potential low-emission fuel for diesel engines but it is not a "drop-in" fuel since diesel engines must be modified for its use and the fueling infrastructure has not been developed (Semelsberger, 2006).

Although methanol has been proposed for many years as a potential liquid fuel for engines it has not been accepted as a fuel since it is highly flammable, toxic and its combustion produces toxic and carcinogenic formaldehyde emissions. Instead, it is used primarily as an intermediate chemical product for the production of liquid fuels or chemicals.

The production of "drop-in" liquid fuels from mixtures of $H_2$ and $CO_2$ typically requires the following processes.
1. The conversion of the $H_2$/$CO_2$ mixture to syngas
2. The conversion of the syngas to fuels that meet ASTM and other fuel specifications. This process usually requires two or more main conversion processes.

In order for $CO_2$ to liquid fuel processes to be commercially viable it is important that manufactured catalysts, for conversion of $H_2$ and $CO_2$ mixtures to syngas and the conversion of this syngas to liquid fuels, meets one or more of the quality and performance specifications listed below in Table 1:

Table 1—Quality and Performance Specifications for the Catalytic Conversion of $H_2/CO_2$ Mixtures to Syngas The catalyst contains low-cost constituents (no [or nominal] rare metals).

It can be economically manufactured in multiple ton quantities.

The catalyst is robust (e.g., Rockwell hardness greater than Mohr 03-04).

It is chemically and physical stable up to about 2,100° F.

It can be loaded readily into catalytic reactors (e.g. tubular or packed bed reactors).

The pressure drop from the top to the bottom of the catalytic reactor is acceptable.

The catalyst activation (e.g., reduction with $H_2$) can be carried out in-situ.

The $CO_2$ to CO conversion efficiency is greater than about 50% per pass, but preferably greater than about 65% per pass at space velocity's of greater than about 10,000 $hr^{-1}$.

The CO production selectivity is greater than about 70%, but preferably greater than about 85%.

It does not coke (e.g. form carbon deposits).

It has a long lifetime and doesn't require systematic re-activation (reduction).

Two approaches have been described in the prior art for the conversion of $CO_2$ to syngas. The first and most widely described approach employs catalytic processes for the conversion of mixtures of $CO_2$ and $H_2$ to syngas. This method is typically referred to as "$CO_2$ hydrogenation" or "reverse water gas shift (RWGS)" (Senderens et al, 1902; Daza et al, 2016; Vogt et al, 2019). The second approach involves electrolysis processes for the conversion of mixtures of $CO_2$ and $H_2O$ to syngas (Wang et al, 2016).

Catalytic Conversion of $H_2/CO_2$ Mixtures to Syngas—Many patent applications, patents and publications describe the development of catalysts for the conversion of $H_2$ and $CO_2$ mixtures to syngas. This prior art is evaluated with respect to the quality and performance specifications outlined in Table 1.

Iwanani et al (1993) developed a catalyst comprised of transition metals with rare metals (such as Ni, Fe, Ru, Rh, Pt, W, Pd, Mo) on zinc oxide for the reduction of $CO_2$ and $H_2$ mixtures to CO. They achieved relatively low conversions of up to 37% without significant loss of catalyst activity after 150 hrs but testing for longer periods was not carried out.

Chen et al (2015) reported the synthesis of a nano intermetallic catalyst ($InNi_3CO_{0.5}$) that proved to be active and selective for the RWGS reaction. The catalyst was fabricated by carburizing the In—Ni intermetallic base which produced dual active sites on the catalyst surface. They achieved a moderate 52-53% $CO_2$ conversion for 150 hrs at 600° C. and gas hourly velocities of 300,000 ml/g (cat)/hr. Testing of this catalyst for longer periods was not carried out.

Bahmanpour et al (2019) found an in situ formed Cu—Al spinel as an active catalyst for the hydrogenation of $CO_2$ with $H_2$ into syngas. They used co-precipitation followed by hydrogen treatment to form the Cu—Al spinel in different weight ratios. A Cu to Al ratio of 4 to 1 was found to be the efficient for $CO_2$ conversion. They maintained a relatively low $CO_2$ conversion rate of 47% at 600° C. at relatively high space velocities and observed no detectable deactivation after a 40 hr. test. However, copper containing catalysts tend to deactivate by sintering at high temperatures. In addition, candidate catalyst formulations need to be tested for 1,000 hrs. or more to assess potential commercial viability.

Electrochemical Conversion of $CO_2/H_2O$ Mixtures to Syngas—The electrochemical conversion of $CO_2$ has been a dynamic field of research (Zhu, 2019). Much of the R&D effort has centered on the modification of fuel cells (Sunfire, 2016) and PEM and alkaline electrolysis systems (Messias et al, 2019).

PEM & Alkaline Electrolysis—Opus 12 has developed a PEM electrolyzer that converts mixtures of $CO_2$ and $H_2O$ to a mixture of sixteen $C_1$-$C_3$ oxygenated hydrocarbons (alcohols, ketones, aldehydes and acids) (Kuhl et al, U.S. Patent Application Publication 2017/0321333). The separation of this complex mixture into specific chemical compounds requires costly refining processes. If that separation is successful, ethanol is the only suitable product that can be used as a fuel (e.g. blended with gasoline).

Fuel Cells—Sunfire has developed a process based on high-temperature co-electrolysis of $CO_2$ and $H_2O$ using solid oxide electrolysis cells (SOEC) to produce syngas. The SOEC operates at high pressure (>1 MPa) and high temperature (>800° C.). The syngas is then converted to long-chain hydrocarbons using traditional Fischer-Tropsch processes. The waxes are converted into gasoline and diesel fuels using a two-step catalytic refining process. Therefore, three-steps are required for Sunfire's production of "drop-in" fuels and this process requires complex wax upgrading or refining.

In the current art, four principal processes for the conversion of $CO_2$ to "drop-in" liquid fuels are possible:

One-Step Processes
1. $CO_2$ is converted directly to liquid fuels using catalytic or electrochemical processes.

Two-Step Processes
1. $CO_2$ is converted to syngas using catalytic or electrochemical processes.
2. The syngas is converted directly to liquid fuels using a second catalyst.

Two-Step Processes
1. $CO_2$ is converted to primary chemical intermediates using catalytic or electrochemical processes;
2. The chemical intermediates are converted directly to liquid fuels using a second catalyst.

Three-Step Processes
1. $CO_2$ is converted to syngas using catalytic or electrochemical processes;
2. The syngas is converted to a primary chemical intermediate (e.g. wax; methanol, etc.);
3. The purified intermediate is converted directly to liquid fuels.

Four-Step Processes
1. $CO_2$ is converted to syngas using catalytic or electrochemical processes;
2. The syngas is converted to a primary chemical intermediate (e.g. wax; methanol, etc.);
3. The purified intermediate is converted to liquid fuels using two major chemical processes Four-Step Processes
1. $CO_2$ is converted to syngas using catalytic or electrochemical processes.
2. The syngas is converted to a mixture of organic intermediates (e.g. wax; methanol, etc.);
3. Separation processes are employed to generate the desired purified intermediate;
4. The purified intermediate is converted to liquid fuels.

In order for these four processes to be commercially viable it is essential that the manufactured catalysts for the production of liquid fuels and the fuel products meet some of the quality and performance specifications outlined in Table 2.

Table 2—Quality and Performance Specifications for the Catalytic Conversion of Syngas to Liquid Fuels 1. The catalyst contains low-cost constituents (no [or nominal] rare metals).
2. It can be economically manufactured in multiple ton quantities.
3. The catalyst is robust (e.g., Rockwell hardness greater than Mohr 03-04).
4. It is chemically and physical stable up to about 1,800° F.
5. It can be loaded readily into catalytic reactors (e.g. tubular reactors).
6. The pressure drop from the top to the bottom of the catalytic rector is acceptable.
7. The catalyst activation (e.g., reduction with $H_2$) can be carried out in-situ.
8. The CO to liquid fuel conversion efficiency is greater than about 35% per pass, preferably around or above 55% per pass.
9. It has a long lifetime and doesn't require systematic re-activation (reduction).
10. The liquid fuels are cost competitive with petroleum derived fuels.
11. The liquid fuels meet fuel standards published by ASTM and other fuel standards organizations.

The prior art for the one-, two-, three-, and four-step processes are summarized and assessed with respect to the quality and performance specifications outlined in Tables #1 and #2.

One-Step Processes—Most of the effort to convert $CO_2$ to liquid hydrocarbon fuels in a single reactor has been to develop a catalyst that first generates CO from $CO_2$ by hydrogenation. The CO then reacts with $H_2$ on the same catalyst to form liquid fuels through a mechanism based on a conventional F-T reaction. One of the challenges associated with this F-T process using $CO_2$ is that there is only a small concentration of CO present during the reaction. This limits chain growth and consequently the product distribution is normally rich in light hydrocarbons, which are not suitable as liquid fuels. To date, most research has focused on the use of iron-based catalysts, which are active for the reverse water gas-shift reaction and F-T chemistry (National Academy of Sciences, 2019).

Landau et al (Australian patent application 2015/203898) described a 20% $Fe_2O_3$ on iron-spinel catalyst. The catalyst particle size varied from 100 um to 3.0 mm. This catalyst was tested using syngas with an $H_2/CO_2$ ratio of 2.0-3.0/1.0, a very low space velocity of about 2.0 $hr^{-1}$, a temperature of 325-350° C., and a pressure of 20-40 atmospheres. The maximum conversion of $CO_2$ was 36%. The selectivity of the products was: CO (13%), $CH_4$ (9%), $C_2$-$C_5$ (44%) and $C_6$-$C_{27}$ HC's (25%). The olefin/paraffin ratio of the $C_6$+ hydrocarbons was about 5/1. This catalyst does not produce a "drop-in" fuel that meets ASTM specifications, and it doesn't meet the catalyst quality and performance specifications listed above.

Wang et al. (2013) described a $Fe/ZrO_2$ catalyst for catalyzing the hydrogenation of $CO_2$ that produced primarily $CH_4$ and $C_2$-$C_4$ paraffins. The selectivity for production of liquid-phase hydrocarbons was very low.

Wei et al. (2018) described an iron-based catalyst for the one-step conversion of $CO_2$ into iso-paraffins. The conversion efficiency of $CO_2$ was only 26% with a CO selectivity of about 17%. Coke (carbon) deposition inside the micropores of the catalyst caused a rapid decline of iso-paraffin yield with time.

Williamson et al. (2019) described the performance of a one-step catalyst comprised of iron nano-particles deposited on carbon nanotubes. The catalysts were calcinated at 400° C. for 1 hour or 570° C. for 40 minutes in air and activated with $H_2$ at 400° C. for 3 hours. The catalysts were tested in laboratory reactors at 370° C. and 221 psi using a $H_2/CO_2$ mixture of 3.0/1.0. The average $CO_2$ conversion was 54% with CO and hydrocarbon selectivity's of 30% and 70%, respectively. The average composition of the hydrocarbon products were 43% $CH_4$, 55% $C_2$-$C_4$ and 2.0% $C_5$+ hydrocarbons.

Pan et al. (2007) described the use of an Rh catalyst supported on carbon nanotubes in a tubular reaction for the production of ethanol from mixtures of $CO_2$ and $H_2$ at a very low space velocity of about 13 $hr^{-1}$. In addition to ethanol, this catalyst produced a complex mixture of oxygenated hydrocarbons including methanol, acetaldehyde, acetone, isopropanol and acetic acid. The problem with this catalyst is that it isn't amenable to scale up to commercial scale due to a high catalytic reactor pressure drop, the low space velocity, and the production of a complex mixture of oxygenated hydrocarbons.

Two-Step Processes—Shulenberger et al (U.S. Pat. No. 8,198,338) described a process for the conversion of $CO_2$ into gasoline. $H_2$ and $CO_2$ (2.0/1.0 molar ratio) were converted to methanol using a $Cu/ZnO/Al_2O_3$ catalyst in a catalytic reactor operated at about 50 bar pressure and 500° C. Since the operating pressure was low, the selectivity for methanol production was only about 10%. The methanol produced from the first catalytic process was fed into another catalytic reactor containing a ZSM-5 catalyst and operated at about 4 bar pressure and 390° C. for the conversion of methanol to gasoline. The conversion efficiency of the two-step process and the chemical and physical composition of the gasoline were not described. However, as based upon the selectivity of methanol production in the first reactor, the selectivity for gasoline production was estimated to be less than 10%.

Three-Step Processes—Sunfire carried out electrolytic conversion of $CO_2$ and $H_2O$ using solid oxide electrolysis cells (SOEC) to produce syngas (Zhu, 2019). The syngas was then converted to long-chain hydrocarbons using traditional Fischer-Tropsch processes. The waxes were converted into gasoline and diesel fuels using a two-step catalytic refining process. Therefore, three-steps were required for Sunfire's production of "drop-in" fuels.

Four-Step Processes—Several four-step processes have been described in the current art. One approach is to produce a chemical intermediate such as methanol from $H_2/CO_2$ mixtures using a one-step process, followed by the conversion of the methanol to gasoline using a three-step process. Another approach is to produce syngas from $H_2/CO_2$ mixtures, followed by the Fischer-Tropsch conversion of the syngas to wax and then a two-step conversion of the wax to liquid fuels.

Kothandaraman et al (2016) used a polyamine (PEMA) in tetrahydrofuran (THF) to capture $CO_2$. Although this amine has good $CO_2$ capture efficiency, amines are known to deactivate catalysts. The captured $CO_2$ was converted to methanol in the solution using a Ruthenium PNP pincer catalyst. This catalyst is a complex of Ruthenium with an organic ligand that surrounds the Ruthenium. This process was tested in the laboratory using a $H_2/CO_2$ reactant ratio of 3.0/1.0, a pressure of 75 atmospheres and a temperature of 145° C. The carbon conversion of $CO_2$ to $CH_3OH$ was 65%.

A plant to demonstrate this process was commissioned in Svartsengi, Iceland during 2012. The $H_2$ is produced electrochemically from $H_2O$ using 5.0 megawatts of geothermal power. The $CO_2$ is captured from the Svartsengi power plant in Iceland. The methanol output is about 50,000 liters/year.

Gasoline can be produced from this methanol using the three-step Exxon-Mobil patented process (Jafari, 2018). This process employs three catalytic reactors: Catalytic conversion #1: methanol to dimethyl ether; Catalytic conversion #2: dimethyl ether to $C_2$-$C_5$ olefins; Catalytic conversion #3: $C_2$-$C_5$ olefins to gasoline. The MTG gasoline is typically comprised of 53% paraffins, 12% olefins, 9% napthenes, 26% aromatics, 0.3% benzene and no sulfur. The octane ratings (RON+MON)/2 are 87 and the RVP (psi) is 9.0.

In conclusion, no prior art has been identified for which "drop-in" liquid fuels can be produced in two primary steps from $CO_2/H_2$ mixtures which meet the performance and quality specifications summarized in Tables 1 and 2.

In comparison to other catalysts developed for this application, the improved catalyst described in this document utilizes only one transition metal, Ni, whereas all other $CO_2$ hydrogenation catalysts employ two or more transition metals (Okado, U.S. Pat. No. 6,423,665; Choudhary, U.S. Pat. No. 7,432,222; Millar, WO 2000/016899). Several other prior art formulations require the use of expensive metals (e.g. Pt, Pd, Rh, Ru and Ir) (Okado, U.S. Pat. No. 6,409,940 and Green, U.S. Pat. No. 5,431,855).

Tail-Gas Conversion—The one-step, two-step, three-step and four-step processes produce tailgas that typically consists of $C_1$-$C_5$ hydrocarbons and $CO_2$ as well as unconverted $H_2$ and CO. This tailgas needs to be either used as energy for a commercial-scale plant or converted to additional syngas.

The predominant process for conversion of tail-gas to syngas is by means of Steam Methane Reforming (SMR) process. However, steam reforming has several disadvantages. It is a highly endothermic reaction and excess steam is required to prevent or delay deactivation from carbon deposition. Consequently, the high energy requirement for SMR results in a high cost of production of this additional synthesis gas. In addition. SMR processes produce $CO_2$ from combustion of fuel gas to fire the burners in the SMR.

Catalytic partial oxidation (POX) of tail-gas to syngas has several advantages over SMR. Since the oxidation of hydrocarbons to synthesis gas mixtures is exothermic, this process is much more energy efficient than both the steam and dry reforming processes (Gaffney et al, U.S. Pat. No. 6,402,989).

However, POX has several potential disadvantages as follows:
 1. Relatively pure oxygen is needed, the source of which is usually from its cryogenic separation from air.
 2. The POX process can be highly exothermic which can lead to catalyst hot spots which can damage the catalyst or causing thermal runaways.

Autothermal reforming (ATR) of tail-gas to syngas is another process that can be used for conversion of the tail-gas. The partial oxidation occurs in the inlet of the reactor, which provides heat for steam reforming reaction. As a result, there is no need to supply heat to the reactor (Ashcroft (1991); Choudhary (1995); and Ruckenstein (1998)).

Cobalt-nickel catalysts on alumina have been found to show superior performance for ATR of methane in terms of activity, stability and synergy when compared to other catalysts. However, some carbon formation is observed when mixtures of $CH_4$, $CO_2$ and $O_2$ are reformed at about 1,300° F. and 15 psi (Foo (2012) and Zhang (2007)).

SUMMARY OF THE INVENTION

In one aspect, the present invention provides a process for the conversion of carbon dioxide into a liquid fuel, wherein the process comprises the steps of: a) introducing a gaseous mixture of carbon dioxide and hydrogen, or a mixture of carbon dioxide, hydrogen and light hydrocarbons, into a first catalytic reactor in a catalytic conversion system to produce syngas, wherein the first catalyst is a solid-solution catalyst that is formed from Nickel and Magnesium, ideally including $Ni_2Mg$; b) introducing the syngas into a second catalytic reactor in the catalytic conversion system to produce tailgas, water and liquid fuel, wherein the second catalyst comprises about 2 to about 25 parts-by-weight of an element wherein the element is selected from a group of elements consisting of cobalt, iron, magnesium, manganese, calcium, barium, copper and zinc, and from about 0.1 to about 5 parts-by-weight of at least one metal selected from a group consisting of cerium, ruthenium, lanthanum, platinum, or rhenium of 0.1 to 5.0 parts per 100 parts-by-weight of a support selected from a group consisting of silica, alumina, and combinations thereof thereby producing liquid fuel, tailgas and water; c) separating the liquid fuel, tailgas and water from one another, thereby producing the liquid fuel.

In another aspect, the present invention provides a catalyst for the conversion of carbon dioxide into syngas, wherein the catalyst is an impregnated, metal-coated spinel comprising about 2 to about 25 parts-by-weight of magnesium having a surface area greater than about 50 m$^2$/g, about 0.1 to about 5 parts-by-weight of cerium, ruthenium, lanthanum, platinum or rhenium, and about 2 wt. % to about 20 wt. % nickel per 100 parts-by-weight of a silica support.

In another aspect, the present invention provides a process for the production of a liquid fuel, wherein the process comprises the steps of: a) separating oxygen from ambient air using a cryogenic air separator; b) mixing the oxygen with natural gas in the presence of heated supercritical carbon dioxide at high pressure and high temperature, thereby combusting the natural gas, producing combustion gases comprising carbon dioxide and water, along with heat; c) passing the combustion gases through a gas turbine generator, thereby generating electricity that is used for at least two purposes, and wherein the at least two purposes are distribution to the electric grid and use in the process for production of the liquid fuel and allowing the combustion gases to exit the gas turbine generator; d) further passing the combustion gases through a heat exchanger, wherein the heat exchanger reduces the temperature of the combustion gases; e) removing water from the combustion gases to provide carbon dioxide; f) introducing a portion of the carbon dioxide along with hydrogen, or a mixture of the carbon dioxide portion with hydrogen and light hydrocarbons, into a first catalytic reactor in a catalytic conversion system to produce syngas, wherein the first catalyst that is a Nickel and Magnesium solid-solution catalyst, ideally the catalyst includes $Ni_2Mg$, and compressing any remaining carbon dioxide while heating it to provide supercritical carbon dioxide; g) introducing the syngas into a second catalytic reactor in the catalytic conversion system to produce tailgas, water and liquid fuel, wherein the second catalyst comprises about 2 to about 25 parts-by-weight of an element wherein the element is selected from a group of elements consisting of cobalt, iron, magnesium, manganese, calcium, barium, copper and zinc, and from about 0.1 to about 5 parts-by-weight of at least one metal selected from a group consisting of cerium, ruthenium, lanthanum, platinum, or rhenium per 100 parts-by-weight of a support selected from a group consisting of silica, alumina, and combinations thereof, thereby producing liquid fuel, tailgas and water; h) separating the liquid fuel, tailgas and water from one another thereby producing the liquid fuel.

In another aspect, the present invention provides a liquid fuel production plant, wherein the plant can produce at least 400 barrels per day of drop-in, synthetic liquid fuel while producing very little $CO_2$ and using less than 80 MW of power, wherein the plant comprises: a) a cryogenic air separator that separates oxygen from ambient air, wherein the cryogenic air separator is connected to a combustions system that uses the oxygen to combust natural gas, producing carbon dioxide and water; b) a gas turbine power generator that is connected to the combustion system, allowing combustion products including gaseous carbon dioxide and water to flow through the gas turbine power generator, producing electricity; c) a heat exchanger connected to the gas turbine power generator, such that gaseous carbon dioxide and water exiting the gas turbine is introduced to the heat exchanger, which cools the gaseous carbon dioxide and water; d) a cooler and mist separator connected to the heat exchanger such that cooled gas from the heat exchanger flows into the cooler and mist separator, thereby removing water from the gas stream and producing carbon dioxide; e) a first catalytic reactor connected to the cooler and mist separator such that the carbon dioxide is introduced into the first catalytic reactor, wherein the first catalyst that is a Nickel and Magnesium solid-solution catalyst, ideally the catalyst includes $Ni_2Mg$, and the first catalytic reactor is capable of producing syngas; f) a second catalytic reactor connected to the first catalytic reactor such that syngas flows from the first catalytic reactor to the second catalytic reactor, wherein the second catalytic reactor comprises a second catalyst, wherein the second catalyst comprises about 2 to about 25 parts-by-weight cobalt and from about 0.1 to about 5 parts-by-weight of at least one metal selected from a group consisting of cerium, ruthenium, lanthanum, platinum, or rhenium per 100 parts-by-weight of a support selected from a group consisting of silica, alumina, and combinations thereof and the second catalytic reactor is capable of producing liquid fuel from syngas.

BRIEF DESCRIPTION OF THE DRAWINGS

FIG. 1 illustrates the process flow diagram for the improved catalysts and processes described herein for the direct production of liquid fuels from $CO_2$ and renewable $H_2$. It further illustrates an integrated conversion system and process for the production of renewable liquid fuels.

FIG. 2 summarizes the desired reactions (201, 203 and 204), and undesirable side reactions (202, 205-213) that can occur when mixtures of $CO_2$ and $H_2$ are catalytically converted to CO.

FIG. 3 shows the effect of operating temperature on the production of CO at 50 psi by catalyst #1 105.

FIG. 4 illustrates the relationship between the operating pressure for catalyst #2 107 and CO conversion efficiency at 450° F.

FIG. 5 illustrates the primary processes for the Allam oxy-fuel combustion process and integration of the direct liquid fuel production process with an Allam Oxy-Fuel Combustion Process.

DETAILED DESCRIPTION OF THE INVENTION

This invention relates to improved catalysts and processes for the efficient and economical conversion of $CO_2$ and $H_2$ mixtures directly to synthetic liquid fuels in two steps.

FIG. 1 illustrates the process flow diagram for the improved catalysts and processes described herein for the direct production of liquid fuels from $CO_2$ and renewable $H_2$. It further illustrates an integrated catalytic converter and process for the production of renewable liquid fuels.

Electrolysis is used to generate $H_2$ 101. The power for $H_2$ production may be generated from, but not limited to, renewable and or low-carbon sources such as wind, solar, geothermal, hydro, ocean currents, biomass, flare-gas, nuclear and others. Other possible sources include low-cost (off-peak) power from traditional fossil fuel power plants or efficient power produced from oxy-combustion plants.

Captured $CO_2$ 102 may be obtained from, but not limited to; fermentation processes; cement plants; traditional power plants; oxy-combustion power plants; ambient air $CO_2$ capture systems; natural gas well-heads, secondary oil recovery processes; and other $CO_2$ sources.

$H_2$ from process 101; $CO_2$ from process 102; and syngas and heat (Q) from process 110 are mixed 103 in the proper proportions, heated, and input into the catalytic conversion system 104. Two innovative catalysts, catalyst #1 105 & catalyst #2 107 are incorporated in the catalytic conversion system 104.

Catalyst #1 105 is the high-surface area Nickel and Magnesium solid-solution catalyst, ideally the catalyst includes $Ni_2Mg$, and the solid-solution catalyst described herein for the efficient conversion of $CO_2$ and $H_2$ mixtures to syngas. This catalyst is a significant improvement over the low-surface area solid-solution catalyst described by Schuetzle et al in U.S. Pat. No. 9,611,145 and Canadian Patents No. 2,936,903 & 2,993,671. The catalytic species described in this prior art was primarily comprised of $Ni^+$ compounds in the lowest possible valence state (e.g. $Ni_2O$ and $Ni_2MgO_2$) before reduction (activation) with $H_2$. $Ni_2O$ is referred to as nickel sub-oxide which has a tetragonal structure (Wagner et al. in U.S. Pat. No. 4,990,491). The reduction of $Ni_2MgO_2$ with $H_2$ produces the active $CO_2$ reforming catalyst $Ni_2Mg$ and the reduction of $Ni_2O$ with $H_2$ at high temperatures in the presence of MgO primarily produces elemental Ni. Since $H_2$ calcining isn't 100% efficient, some Ni and $Ni_2MgO_2$ is still present.

The improvements described herein include a manufacturing process that produces robust catalysts comprised primarily of $Ni_2Mg$ and that have an increased surface area by about ten times greater than that described in the prior art.

Catalyst #2 107 is a catalyst that was developed for the direct production of liquid fuels from syngas as described by Schuetzle et al in U.S. Pat. Nos. 8,394,862; 9,090,831; and 9,631,147. Catalyst #1 105 and catalyst #2 107 have been developed to operate at about the same pressures in the range of about 50 to 350 psi.

Since catalyst #1 operates at a higher temperature than catalyst #2, a heat exchanger 106 is incorporated in the catalytic conversion system 104 to reduce the temperature of the gases to the operating temperature of catalyst #2 107. The products from the catalytic conversion processes 104 are separated by a product separator 108 into tailgas 109, water 111, and renewable liquid fuels 113.

Some of the tailgas 109 is recycled back to the catalytic conversion process 104 until the CO in the syngas reaches the desired conversion efficiency. The remaining tailgas 109 is combusted 110 with oxygen (Autothermal Reforming (ATR)) produced from the electrolysis system 101. The products from the ATR process 110 are syngas and heat. The syngas is blended with the other gases in 103 and the heat from 110 is used to help heat the gas blending/heating system 103. Additional heat is added to the gas blending system 103 to bring the gases to a temperature up to the operating temperature of catalyst #1 105.

The water (commonly referred to as catalyst reaction water) 111 can be used for greywater applications 112, or purified for the electrolysis process 101 and/or other uses. The renewable liquid fuel 113 can be used directly (neat) for off-road diesel engines 114, blended with petroleum derived diesel fuel 115, or distilled 116 into premium fuel products (e.g., #1 diesel, #2 diesel, #3 diesel and jet fuels) 117.

FIG. 2 summarizes the potential reactions that can occur when mixtures of $CO_2$ and $H_2$ are catalytically converted to CO. The catalyst described in this improved art has been developed to primary produce CO by way of reactions 201 from mixtures of $CO_2$ and $H_2$ and $CO_2$ and $C_1$-$C_8$ hydrocarbons via reactions 203 and 204 if present with the $CO_2$).

The improved catalyst and processes primarily produces CO from $CO_2$ and $H_2$ (reaction 201) or CO from $CO_2$ and hydrocarbons (reactions 203 and 204). These reactions are endothermic which means that heat needs to be added for the conversion to occur. As illustrated in FIG. 1, the first catalyst in the catalytic reactor is used to efficiently convert mixtures of $CO_2$ and $H_2$ to CO. This improved $CO_2$ reforming catalyst 105 predominantly produces CO with greater than about 90% selectivity under low pressure operating conditions (<350 psi).

FIG. 3 shows the effect of operating temperature on the production of CO from $CO_2$ at 50 psi by this improved $CO_2$ reforming catalyst. The conversion of $CO_2$ increases exponentially with temperature from about 750 to 1,300° F. The conversion of $CO_2$ then levels off from about 1,300 to 1,700° F. which follows a power fit (y=0.45x−309). The $CO_2$ conversion efficiency is about 75% with a CO production selectivity of about 100% at 1,700° F.

Table 3 summarizes the selectivity's for CO and $CH_4$ production from $CO_2$ at about 1,600° F. and 50 psi for the $CO_2$ reforming catalyst. The $CO_2$ conversion efficiency is about 72% with selectivity for CO of about 100%. No other products are formed under these conditions such as the formation of $CH_4$ (reactions 202 and 205); and carbon (reactions 209, 210, 211, 212 and 213). Reactions 206, 207 and 208 are very minor since the concentration of $H_2O$ in the $CO_2/H_2$ stream is very low.

TABLE 3

The Selectivity's for CO and $CH_4$ Production at about 1,600° F. and 50 psi for the Improved $CO_2$ Reforming Catalyst
$CO_2$ Reforming Catalyst

| Component | Conversion (%) | Selectivity (%) |
|---|---|---|
| $CO_2$ | −72.0 | — |
| CO | +72.0 | 100 |
| $CH_4$ | 0.0 | 0.0 |

Table 4 summarizes the effect of pressure on the conversion of $CO_2$ to CO at 1,600° F. As the pressure is increased from 50 to 300 psi, the CO selectivity decreases from about 100% to 89% whereas the $CH_4$ selectivity increases from 0% to 11%. This change in pressure doesn't have any effect on the conversion efficiency of $CO_2$.

TABLE 4

The Effect of Operating Pressure on the Conversion Efficiency of $CO_2$ to CO at 1,600° F. for the Improved $CO_2$ Reforming Catalyst

| Pressure (psi) | $CO_2$ Conversion (%) | CO Selectivity (%) | $CH_4$ Selectivity (%) | Other Products (%) |
|---|---|---|---|---|
| 50 | −72.0% | 100% | 0% | 0 |
| 150 | −72.0% | 98% | 2% | 0 |
| 300 | −71.0% | 89% | 11% | 0 |

The second catalyst 107 in the back end of the converter (FIG. 1) utilizes the Greyrock direct fuel production catalyst described previously by Schuetzle et al in U.S. Pat. Nos. 8,394,862 & 9,909,071 which has been improved in this process to operate efficiently down to about 50 psi.

This composition of the improved catalyst 107 contains from about 2 to about 25 parts-by-weight cobalt and from about 0.1 to about 5 parts-by-weight of at least one metal selected from a group consisting of cerium, ruthenium, lanthanum, platinum, or rhenium per 100 parts-by-weight of a support selected from a group consisting of silica, alumina, and combinations thereof. This catalyst is produced commercially using stationary calcining ovens so that the catalyst particle aspect ratio (ratio of length to width), surface area, sub-surface and surface pore size distribution, pore volume, and catalyst crystallinity are maintained within about 5% of specifications.

FIG. 4 illustrates the relationship between the operating pressure for catalyst #2 107 and CO conversion efficiency at 450° F. The % change in CO conversion rate was found to follow the relationship given by Eq. 2 in which in which $P_1$ and $P_2$ are the pressures to be compared:

$$\% \text{ Change in CO conversion rate} = (P_1/P_2)^{0.5} \qquad \text{Eq. 2}$$

Since the first catalyst operates at a higher temperature than the second catalyst, a heat exchanger (FIG. 1-106) is incorporated between the catalysts to reduce the temperature of the second catalyst to its ideal operating level.

A foremost advantage of this process is that catalysts #1 and #2 can be operated efficiently in tandem at the same pressure which eliminates the need for compression between the two catalytic reactors.

Table #5 provides the relationship between the temperatures of catalyst #2 on the conversion of $CO_2$ in syngas produced from catalyst #1. Therefore, catalyst #2 converts some of the $CO_2$ not converted by catalyst #1.

TABLE 5

The Effect of Temperature on the Conversion of $CO_2$ in Syngas by Catalyst #2

| T (° F.) | $CO_2$ Conversion (%) |
|---|---|
| 400 | 1.71 |
| 410 | 3.23 |
| 420 | 5.39 |
| 430 | 9.25 |

TABLE 5-continued

The Effect of Temperature on the Conversion
of $CO_2$ in Syngas by Catalyst #2

| T (° F.) | $CO_2$ Conversion (%) |
|---|---|
| 440 | 14.6 |
| 450 | 24.5 |

Since the conversion of $CO_2$ at 1,600° F. and 150 psi is 72% efficient (Table 3), the resulting syngas contains about 28% $CO_2$. Therefore, when catalyst #2 is operated at 450° F., about 25% of the incoming syngas to catalyst #2 is converted to $CO_2$ resulting in tailgas that contains 34.1% $H_2$, 17.1% CO, 23.1% $CH_4$ and 25.6% $CO_2$.

Table 6 summarizes the products that are produced under two different pressure operating conditions. When $H_2/CO_2$ mixtures (2.2/1.0) are input into the improved $CO_2$ reforming catalyst, operated at 300 psi and 1,600° F., it produces syngas with an $H_2/CO$ ratio of about 2.0-2.3/1.0.

When this syngas is input into the direct fuel production catalyst operated at 415° F. and 300 psi, liquid fuels ($C_5$-$C_{23}$ hydrocarbons) are produced with a single pass selectivity of 47.5%. The side products include gas-phase $C_1$-$C_4$ hydrocarbons, solid-phase $C_{24}$+ hydrocarbons, and unreacted $CO_2$ with selectivities of 21.2%, 2.5% and 25.8%, respectively.

TABLE 6

The Effect of Catalyst Operating Conditions on the Catalytic
Converter Operating Conditions Employed for the Production of Synthetic
Liquid Fuel from $H_2/CO_2$ Mixtures (2.2/1.0)

| CO2 Reforming Catalyst #1 Conditions | | Fuel Production Catalyst #2 Conditions | | Single Pass Product Selectivities (%) | | | |
|---|---|---|---|---|---|---|---|
| | | | | | Fuel | | |
| Temp. (° F.) | P (psi) | T (° F.) | P (psi) | $C_1$-$C_4$ HC's | ($C_5$-$C_{23}$ HC's) | ($C_{24}$+ HC's) | ($CO_2$) |
| 1,600 | 300 | 415 | 300 | 24.2 | 47.5 | 2.5 | 25.8 |

The $CO_2$ used as inputs to the process can be obtained from many different sources including ambient air, fermentation processes, cement plants, conventional power plants, oxy-combustion processes, biogas, gases recovered from secondary oil production processes, and so forth.

$CO_2$ containing $C_2$-$C_6$ hydrocarbons can also be used as process inputs since these hydrocarbons will also be converted to liquid fuels or methane. Such streams include natural gas condensates, gases from refinery processes and other gas streams that contain $CO_2$ and light hydrocarbons.

The integrated process above requires a carbon dioxide input. In one embodiment, the carbon dioxide is supplied from the separation of the carbon dioxide in a flue gas stream using an alkylamine. Alkylamines used in the process can include mono-ethanolamine, diethanolamine, methyl-di-ethanolamine, disopropyl-amine, amino-ethoxy-ethanol, or combinations thereof. In another embodiment, the carbon dioxide is already present in natural gas feedstocks.

The manufacturing process for the first catalyst is important in that it produces a catalyst that forms a unique solid solution phase, bi-metallic crystalline phase that leads to no segregation of the metal phases. This unique chemical structure leads to enhanced resistance to coking, when compared to conventional metal supported reforming catalysts. This also leads to enhanced resistance to syngas poisons such as sulfur and ammonia. In addition, this catalyst has enhanced catalytic activity at lower surface area compared to monometallic segregated catalyst phase, for example Ni on alumina. This catalyst requires no alkali promotion needed to curb the carbon deposition typically seen with feed gases as described herein. The catalyst is also operable in a variety of dry, steam, combined dry/steam and tri-reforming feeds. Mixes of higher hydrocarbon feedstocks are also achievable with this catalyst.

The manufacture of the improved $CO_2$ hydrogenation catalyst may involve some or all of the following steps that will achieve an effective and economical commercial solid solution catalyst:

a. Synthesis of high surface area (>50 m$^2$/g) metal-spinels which may consist of a Co-alumina spinel, a Fe-alumina spinel, an Mg-alumina spinel, a Mn-alumina spinel, a Ca-alumina spinel, a Ba-alumina spinel, a Cu-alumina spinel, or a Zn-alumina spinel.

b. Modification of the above spinels with impregnation of up to 20 wt. % of additional Fe, Mg, Mn, Ca, Ba, Cu or Zn that is not chemically bonded with one or more the spinels listed in above.

c. The impregnation of the metal-coated spinels with a solution that is comprised of mixture of water soluble nickel salts and rare-earth metal salts (e.g., nitrates or acetates).

d. The calcining of the metal-coated spinels at temperatures up to 2,100° F.

e. Additional impregnation and calcining as required producing an impregnated spinel that is comprised of 2-20 wt. % Ni and 0.1-5.0 wt. % of the rare-earth metals.

$CO_2$ Sources—Carbon capture is the process of capturing $CO_2$ from point sources. The pioneering catalytic converter and process described herein requires that the $CO_2$ feedstock can be captured efficiently and economical with minor levels of contaminants.

Several methods have been developed for the collection of $CO_2$ from fermentation processes, traditional power plants, oxy-combustion power plants, cement plants, and $CO_2$/hydrocarbon streams from biogas sources, refineries and secondary oil recovery processes (Schuetzle et. al., 2010).

Power plants typically employ control devices for removing sulfur oxides and particulates. The addition of carbon capture systems requires a large additional capital cost and increased parasitic power. As a result, removal in conventional power plants can increase the cost of electricity by 50% to 70% (IGCC, 2005). The cost of capturing $CO_2$ emissions from coal power plants and natural gas power plants averages $130/ton and $95/ton, respectively (Metz et. al, 2005).

Oxy-combustion power plants have the potential of produce high-quality $CO_2$ at a low cost. NET Power is a leader in the development and deployment of these power plants (Allam et al, 2017). NET Power has developed and deployed a novel power generation system that produces electricity from natural gas with a net energy efficiency of about 59% at a cost that is competitive with current technologies, and which generates zero atmospheric emissions.

The NET Power system is based on a new thermodynamic cycle called the Allam Cycle (Allam et al, 2013). It uses a high-pressure, highly recuperative, oxyfuel, supercritical $CO_2$ cycle that makes emission capture a part of the core power generation process. The result is high-efficiency power generation that inherently produces a $CO_2$ byproduct at no additional cost to the system's performance. The $CO_2$ produced from this oxy-combustion process is an ideal feedstock for the production of ultra-low carbon liquid fuels by this catalytic converter and process.

Fermentation processes are used to produce distillates, wine, beer and ethanol fuels. As shown in Table 7, $CO_2$ is the primary constituent in fermentation process emissions. The concentration of ethanol is low, ranging from about 2,000-4,000 ppm. Since fermentation is an anaerobic process, $O_2$ is typically not present. Small quantities of sulfur compounds such as $H_2S$ and $SO_2$ may be present at low concentrations (Safriet, 1995).

TABLE 7

Typical Concentration of Constituents in Fermentation Process Emissions

| Constituent | Concentration |
| --- | --- |
| $CO_2$ | 99.6% |
| Ethanol | 3,000-4,000 ppm |
| $H_2S$ | 1.1 ppm |
| $SO_2$ | <0.2 ppm |
| $O_2$ | <0.1 ppm |

Since the concentrations of the contaminants are low, this is an ideal source of $CO_2$ for the improved direct fuel production process described in this invention. The low concentrations of sulfur compounds are easily removed using conventional adsorbents. The captured $CO_2$ cost can range from $5/ton to about $35/ton. The second catalyst in the catalytic reactor will convert most (>50 mole %) of the ethanol to liquid fuels.

The cement industry currently represents about 7% of the carbon dioxide ($CO_2$) emissions globally and is the third-largest industrial energy consumer. Cement production involves the decomposition of limestone (calcium carbonate), which represents about two-thirds of the total $CO_2$ emissions generated in the process, with the remainder of $CO_2$ emissions being due the combustion of fuels. This industry has the second-largest share of total direct industrial carbon dioxide ($CO_2$) emissions, at 27% (2.2 gigatons) of carbon dioxide per year [$GtCO_2$/yr.] in 2014 (IEA, 2018).

Cement plant emissions contain $CO_2$ at about 25 volume %. Amine (MEA) based absorption capture technology currently costs about $90/ton. If oxy-fuel is employed for heating then the cost drops to about $50/ton of $CO_2$ (Gardarsdottir et al., 2019). However, this cost can be much higher if significant cement plant modifications are required. The captured $CO_2$ from cement plants using amine capture or oxy-fuel combustion is an ideal feedstock for the production of renewable fuels from this catalytic converter and process.

Once $CO_2$ is captured it must be compressed to high pressures for storage in large vessels or cooled to produce liquid $CO_2$ which is stored in insulated containers. Therefore, if the captured $CO_2$ is directly converted to liquid fuels at the plant site, these costs are eliminated.

Several technologies have been developed to collect $CO_2$ from ambient air (U.S. Pat. No. 9,095,813 B2). The challenges with these ambient air collection processes is that the cost of $CO_2$ collection is very high, with current costs ranging from $400-600/metric ton or higher, however costs may decline as these technologies are commercialized.

There are some $CO_2$ sources that are associated with significant levels of $C_1$-$C_6$ hydrocarbons. Some examples of such sources include $CO_2$/light hydrocarbon mixtures from natural gas well heads, emissions from secondary oil recovery using $CO_2$ and biogas.

Injection of $CO_2$ into oil reservoirs is a common method of secondary oil recovery. After $CO_2$ injection, the recovered $CO_2$ contains light hydrocarbons which need to be separated before $CO_2$ re-injection. U.S. Pat. No. 9,159,105 describes a process for separating the light hydrocarbons from $CO_2$ using an air capture unit. The $CO_2$ is re-injected into the well for additional oil recovery and the light hydrocarbons are used as a fuel for local use.

Various Embodiments

Processes

1. A process for the conversion of carbon dioxide into a liquid fuel, wherein the process comprises the steps of: a) introducing a gaseous mixture of carbon dioxide and hydrogen, or a mixture of carbon dioxide, hydrogen and light hydrocarbons, into a first catalytic reactor in a catalytic conversion system to produce syngas, wherein the first catalyst that is a Nickel and Magnesium solid-solution catalyst, ideally the catalyst includes $Ni_2Mg$; b) introducing the syngas into a second catalytic reactor in the catalytic conversion system to produce tailgas, water and liquid fuel, wherein the second catalyst comprises about 2 to about 25 parts-by-weight of an element wherein the element is selected from a group of elements consisting of cobalt, iron, magnesium, manganese, calcium, barium, copper and zinc, and from about 0.1 to about 5 parts-by-weight of at least one metal selected from a group consisting of cerium, ruthenium, lanthanum, platinum, or rhenium per 100 parts-by-weight of a support selected from a group consisting of silica, alumina, and combinations thereof thereby producing liquid fuel, tailgas and water; c) separating the liquid fuel, tailgas and water from one another thereby producing the liquid fuel.

2. The process according to process 1 above, wherein the syngas is introduced into a heat exchanger to reduce the temperature of the syngas before it is introduced into the second catalytic reactor.

3. The process according to process 1 above, wherein the carbon dioxide introduced into the first catalytic reactor is obtained from a source, wherein the source is selected from a group of sources consisting of oxy-combustion power plants, ambient air $CO_2$ capture systems, natural gas well-heads and secondary oil recovery processes.

4. The process according to process 1 above, wherein the hydrogen is generated using electrolysis, wherein the power for the electrolysis is generated from a renewable or low-carbon source, and wherein the renewable or low carbon source is selected from a group of sources consisting of wind, solar, geothermal, hydro, ocean currents, biomass, flare gas, nuclear, off-peak power from a fossil fuel plant, and power produced by an oxy-combustion plant.

5. The process according to process 1 above, wherein the tailgas is recycled back to the catalytic conversion system.

6. The process according to process 1 above, wherein the water is used for greywater applications.

7. The process according to process 1 above, wherein the second catalytic reactor is operated at a pressure from about 50 psi to about 400 psi, from about 50 psi to about 300 psi, from about 50 psi to about 200 psi, from about 50 psi to about 150 psi, or from about 50 psi to about 100 psi.

8. The process according to process 1 above, wherein the tailgas is partially combusted with oxygen from an electrolysis system used to generate the hydrogen to produce syngas and heat, and wherein the syngas is mixed with the other gases introduced into the second catalytic reactor.

9. The process according to process 1 above, wherein the liquid fuel is used without further processing as fuel for off-road diesel engines.

10. The process according to process 1 above, wherein the liquid fuel is blended with petroleum diesel fuel to provide a fuel blend.

11. The process according to process 1 above, wherein the liquid fuel is distilled to provide #1 diesel, #2 diesel, #3 diesel or jet fuel.

12. The process according to process 1 above, wherein the first catalyst is synthesized by a process comprising the steps of: a) synthesizing at least one metal spinel having a surface area greater than about 50 $m^2/g$ wherein the metal spinel is selected from a group consisting of a Co-alumina spinel, a Fe-alumina spinel, an Mg-alumina spinel, a Mn-alumina spinel, a Ca-alumina spinel, a Ba-alumina spinel, a Cu-alumina spinel and a Zn-alumina spinel; b) coating the spinel with about 1 wt. % to about 20 wt. % of an additional chemical element that is not chemically bonded to the spinel to provide a metal-coated spinel, wherein the additional chemical element is selected from a group consisting of Co, Fe, Mg, Mn, Ca, Ba, Cu or Zn; c) impregnating the metal-coated spinel with a solution comprising water soluble nickel salts and either nitrate or acetate salts of rare-earth metals; d) calcining the impregnated, metal-coated spinel at a temperature up to 2,100° F., thereby synthesizing the first catalyst that is an impregnated spinel that is comprised of about 2 wt. % to about 20 wt. % nickel and of about 0.1 wt. % to about 5.0 wt. % of the rare earth metals.

13. The process according to process 1 above, wherein the first catalyst is synthesized by a process comprising the steps of: a) synthesizing a Co-alumina spinel having a surface area greater than about 50 $m^2/g$; b) coating the spinel with about 1 wt. % to about 20 wt. % of Co to provide a metal-coated spinel; c) impregnating the metal-coated spinel with a solution comprising water soluble nickel salts and either nitrate or acetate salts of rare-earth metals; d) calcining the impregnated, metal-coated spinel at a temperature up to 2,100° F., thereby synthesizing the first catalyst that is an impregnated spinel that is comprised of about 2 wt. % to about 20 wt. % nickel and of about 0.1 wt. % to about 5.0 wt. % of the rare earth metals.

14. The process according to process 1 above, wherein the first catalyst is synthesized by a process comprising the steps of: a) synthesizing a Fe-alumina spinel having a surface area greater than about 50 $m^2/g$; b) coating the spinel with about 1 wt. % to about 20 wt. % of Fe to provide a metal-coated spinel; c) impregnating the metal-coated spinel with a solution comprising water soluble nickel salts and either nitrate or acetate salts of rare-earth metals; d) calcining the impregnated, metal-coated spinel at a temperature up to 2,100° F., thereby synthesizing the first catalyst that is an impregnated spinel that is comprised of about 2 wt. % to about 20 wt. % nickel and of about 0.1 wt. % to about 5.0 wt. % of the rare earth metals.

15. The process according to process 1 above, wherein the first catalyst is synthesized by a process comprising the steps of: a) synthesizing a Mg-alumina spinel having a surface area greater than about 50 $m^2/g$; b) coating the spinel with about 1 wt. % to about 20 wt. % of Mg to provide a metal-coated spinel; c) impregnating the metal-coated spinel with a solution comprising water soluble nickel salts and either nitrate or acetate salts of rare-earth metals; d) calcining the impregnated, metal-coated spinel at a temperature up to 2,100° F., thereby synthesizing the first catalyst that is an impregnated spinel that is comprised of about 2 wt. % to about 20 wt. % nickel and of about 0.1 wt. % to about 5.0 wt. % of the rare earth metals.

16. The process according to process 1 above, wherein the first catalyst is synthesized by a process comprising the steps of: a) synthesizing an Mn-alumina spinel having a surface area greater than about 50 $m^2/g$; b) coating the spinel with about 1 wt. % to about 20 wt. % of Mn to provide a metal-coated spinel; c) impregnating the metal-coated spinel with a solution comprising water soluble nickel salts and either nitrate or acetate salts of rare-earth metals; d) calcining the impregnated, metal-coated spinel at a temperature up to 2,100° F., thereby synthesizing the first catalyst that is an impregnated spinel that is comprised of about 2 wt. % to about 20 wt. % nickel and of about 0.1 wt. % to about 5.0 wt. % of the rare earth metals.

17. The process according to process 1 above, wherein the first catalyst is synthesized by a process comprising the steps of: a) synthesizing a Ca-alumina spinel having a surface area greater than about 50 $m^2/g$; b) coating the spinel with about 1 wt. % to about 20 wt. % of Ca to provide a metal-coated spinel; c) impregnating the metal-coated spinel with a solution comprising water soluble nickel salts and either nitrate or acetate salts of rare-earth metals; d) calcining the impregnated, metal-coated spinel at a temperature up to 2,100° F., thereby synthesizing the first catalyst that is an impregnated spinel that is comprised of about 2 wt. % to about 20 wt. % nickel and of about 0.1 wt. % to about 5.0 wt. % of the rare earth metals.

18. The process according to process 1 above, wherein the first catalyst is synthesized by a process comprising the steps of: a) synthesizing a Ba-alumina spinel having a surface area greater than about 50 $m^2/g$; b) coating the spinel with about 1 wt. % to about 20 wt. % of Ba to provide a metal-coated spinel; c) impregnating the metal-coated spinel with a solution comprising water soluble nickel salts and either nitrate or acetate salts of rare-earth metals; d) calcining the impregnated, metal-coated spinel at a temperature up to 2,100° F., thereby synthesizing the first catalyst that is an impregnated spinel that is comprised of about 2 wt. % to about 20 wt. % nickel and of about 0.1 wt. % to about 5.0 wt. % of the rare earth metals.

19. The process according to process 1 above, wherein the first catalyst is synthesized by a process comprising the steps of: a) synthesizing a Cu-alumina spinel having a surface area greater than about 50 $m^2/g$; b) coating the spinel with about 1 wt. % to about 20 wt. % of Cu to provide a metal-coated spinel; c) impregnating the metal-coated spinel with a solution comprising water soluble nickel salts and either nitrate or acetate salts of rare-earth metals; d) calcining the impregnated, metal-coated spinel at a temperature up to 2,100° F., thereby synthesizing the first catalyst that is an impregnated spinel that is comprised of about 2 wt. % to about 20 wt. % nickel and of about 0.1 wt. % to about 5.0 wt. % of the rare earth metals.

20. The process according to process 1 above, wherein the first catalyst is synthesized by a process comprising the steps of: a) synthesizing a Zn-alumina spinel having a surface area greater than about 50 $m^2/g$; b) coating the spinel with about 1 wt. % to about 20 wt. % of Zn to provide a metal-coated spinel; c) impregnating the metal-coated spinel with a solution comprising water soluble nickel salts and either nitrate or acetate salts of rare-earth metals; d) calcining the impregnated, metal-coated spinel at a temperature up to 2,100° F., thereby synthesizing the first catalyst that is an impregnated spinel that is comprised of about 2 wt. % to about 20 wt. % nickel and of about 0.1 wt. % to about 5.0 wt. % of the rare earth metals.

21. The process according to process 1 above, wherein the first catalyst is an impregnated, metal-coated spinel comprising about 2 to about 25 parts-by-weight of cobalt having a surface area greater than about 50 m$^2$/g, wherein the first catalyst further comprises about 2 wt. % to about 20 wt. % nickel.

22. The process according to process 1 above, wherein the first catalyst is an impregnated, metal-coated spinel comprising about 2 to about 25 parts-by-weight of iron having a surface area greater than about 50 m$^2$/g, wherein the first catalyst further comprises about 2 wt. % to about 20 wt. % nickel.

23. The process according to process 1 above, wherein the first catalyst is an impregnated, metal-coated spinel comprising about 2 to about 25 parts-by-weight of magnesium having a surface area greater than about 50 m$^2$/g, wherein the first catalyst further comprises about 2 wt. % to about 20 wt. % nickel.

24. The process according to process 1 above, wherein the first catalyst is an impregnated, metal-coated spinel comprising about 2 to about 25 parts-by-weight of manganese having a surface area greater than about 50 m$^2$/g, wherein the first catalyst further comprises about 2 wt. % to about 20 wt. % nickel.

25. The process according to process 1 above, wherein the first catalyst is an impregnated, metal-coated spinel comprising about 2 to about 25 parts-by-weight of calcium having a surface area greater than about 50 m$^2$/g, wherein the first catalyst further comprises about 2 wt. % to about 20 wt. % nickel.

26. The process according to process 1 above, wherein the first catalyst is an impregnated, metal-coated spinel comprising about 2 to about 25 parts-by-weight of barium having a surface area greater than about 50 m$^2$/g, wherein the first catalyst further comprises about 2 wt. % to about 20 wt. % nickel.

27. The process according to process 1 above, wherein the first catalyst is an impregnated, metal-coated spinel comprising about 2 to about 25 parts-by-weight of copper having a surface area greater than about 50 m$^2$/g, wherein the first catalyst further comprises about 2 wt. % to about 20 wt. % nickel.

28. The process according to process 1 above, wherein the first catalyst is an impregnated, metal-coated spinel comprising about 2 to about 25 parts-by-weight of zinc having a surface area greater than about 50 m$^2$/g, wherein the first catalyst further comprises about 2 wt. % to about 20 wt. % nickel.

Catalyst

1. A catalyst for the conversion of carbon dioxide into syngas, wherein the catalyst is an impregnated, metal-coated spinel comprising about 2 to about 25 parts-by-weight of cobalt having a surface area greater than about 50 m$^2$/g, about 0.1 to about 5 parts-by-weight of cerium, about 2 wt. % to about 20 wt. % nickel per 100 parts-by-weight of an alumina support.

2. A catalyst for the conversion of carbon dioxide into syngas, wherein the catalyst is an impregnated, metal-coated spinel comprising about 2 to about 25 parts-by-weight of cobalt having a surface area greater than about 50 m$^2$/g, about 0.1 to about 5 parts-by-weight of ruthenium, about 2 wt. % to about 20 wt. % nickel per 100 parts-by-weight of an alumina support.

3. A catalyst for the conversion of carbon dioxide into syngas, wherein the catalyst is an impregnated, metal-coated spinel comprising about 2 to about 25 parts-by-weight of cobalt having a surface area greater than about 50 m$^2$/g, about 0.1 to about 5 parts-by-weight of lanthanum, about 2 wt. % to about 20 wt. % nickel per 100 parts-by-weight of an alumina support.

4. A catalyst for the conversion of carbon dioxide into syngas, wherein the catalyst is an impregnated, metal-coated spinel comprising about 2 to about 25 parts-by-weight of cobalt having a surface area greater than about 50 m$^2$/g, about 0.1 to about 5 parts-by-weight of platinum, about 2 wt. % to about 20 wt. % nickel per 100 parts-by-weight of an alumina support.

5. A catalyst for the conversion of carbon dioxide into syngas, wherein the catalyst is an impregnated, metal-coated spinel comprising about 2 to about 25 parts-by-weight of cobalt having a surface area greater than about 50 m$^2$/g, about 0.1 to about 5 parts-by-weight of rhenium, about 2 wt. % to about 20 wt. % nickel per 100 parts-by-weight of an alumina support.

6. A catalyst for the conversion of carbon dioxide into syngas, wherein the catalyst is an impregnated, metal-coated spinel comprising about 2 to about 25 parts-by-weight of cobalt having a surface area greater than about 50 m$^2$/g, about 0.1 to about 5 parts-by-weight of cerium, about 2 wt. % to about 20 wt. % nickel per 100 parts-by-weight of a silica support.

7. A catalyst for the conversion of carbon dioxide into syngas, wherein the catalyst is an impregnated, metal-coated spinel comprising about 2 to about 25 parts-by-weight of cobalt having a surface area greater than about 50 m$^2$/g, about 0.1 to about 5 parts-by-weight of ruthenium, about 2 wt. % to about 20 wt. % nickel per 100 parts-by-weight of a silica support.

8. A catalyst for the conversion of carbon dioxide into syngas, wherein the catalyst is an impregnated, metal-coated spinel comprising about 2 to about 25 parts-by-weight of cobalt having a surface area greater than about 50 m$^2$/g, about 0.1 to about 5 parts-by-weight of lanthanum, about 2 wt. % to about 20 wt. % nickel per 100 parts-by-weight of a silica support.

9. A catalyst for the conversion of carbon dioxide into syngas, wherein the catalyst is an impregnated, metal-coated spinel comprising about 2 to about 25 parts-by-weight of cobalt having a surface area greater than about 50 m$^2$/g, about 0.1 to about 5 parts-by-weight of platinum, about 2 wt. % to about 20 wt. % nickel per 100 parts-by-weight of a silica support.

10. A catalyst for the conversion of carbon dioxide into syngas, wherein the catalyst is an impregnated, metal-coated spinel comprising about 2 to about 25 parts-by-weight of cobalt having a surface area greater than about 50 m$^2$/g, about 0.1 to about 5 parts-by-weight of rhenium, about 2 wt. % to about 20 wt. % nickel per 100 parts-by-weight of a silica support.

11. A catalyst for the conversion of carbon dioxide into syngas, wherein the catalyst is an impregnated, metal-coated spinel comprising about 2 to about 25 parts-by-weight of iron having a surface area greater than about 50 m$^2$/g, about 0.1 to about 5 parts-by-weight of cerium, about 2 wt. % to about 20 wt. % nickel per 100 parts-by-weight of an alumina support.

12. A catalyst for the conversion of carbon dioxide into syngas, wherein the catalyst is an impregnated, metal-coated spinel comprising about 2 to about 25 parts-by-weight of iron having a surface area greater than about 50 m$^2$/g, about 0.1 to about 5 parts-by-weight of ruthenium, about 2 wt. % to about 20 wt. % nickel per 100 parts-by-weight of an alumina support.

13. A catalyst for the conversion of carbon dioxide into syngas, wherein the catalyst is an impregnated, metal-coated spinel comprising about 2 to about 25 parts-by-weight of iron having a surface area greater than about 50 $m^2/g$, about 0.1 to about 5 parts-by-weight of lanthanum, about 2 wt. % to about 20 wt. % nickel per 100 parts-by-weight of an alumina support.

14. A catalyst for the conversion of carbon dioxide into syngas, wherein the catalyst is an impregnated, metal-coated spinel comprising about 2 to about 25 parts-by-weight of iron having a surface area greater than about 50 $m^2/g$, about 0.1 to about 5 parts-by-weight of platinum, about 2 wt. % to about 20 wt. % nickel per 100 parts-by-weight of an alumina support.

15. A catalyst for the conversion of carbon dioxide into syngas, wherein the catalyst is an impregnated, metal-coated spinel comprising about 2 to about 25 parts-by-weight of iron having a surface area greater than about 50 $m^2/g$, about 0.1 to about 5 parts-by-weight of rhenium, about 2 wt. % to about 20 wt. % nickel per 100 parts-by-weight of an alumina support.

16. A catalyst for the conversion of carbon dioxide into syngas, wherein the catalyst is an impregnated, metal-coated spinel comprising about 2 to about 25 parts-by-weight of iron having a surface area greater than about 50 $m^2/g$, about 0.1 to about 5 parts-by-weight of cerium, about 2 wt. % to about 20 wt. % nickel per 100 parts-by-weight of a silica support.

17. A catalyst for the conversion of carbon dioxide into syngas, wherein the catalyst is an impregnated, metal-coated spinel comprising about 2 to about 25 parts-by-weight of iron having a surface area greater than about 50 $m^2/g$, about 0.1 to about 5 parts-by-weight of ruthenium, about 2 wt. % to about 20 wt. % nickel per 100 parts-by-weight of a silica support.

18. A catalyst for the conversion of carbon dioxide into syngas, wherein the catalyst is an impregnated, metal-coated spinel comprising about 2 to about 25 parts-by-weight of iron having a surface area greater than about 50 $m^2/g$, about 0.1 to about 5 parts-by-weight of lanthanum, about 2 wt. % to about 20 wt. % nickel per 100 parts-by-weight of a silica support.

19. A catalyst for the conversion of carbon dioxide into syngas, wherein the catalyst is an impregnated, metal-coated spinel comprising about 2 to about 25 parts-by-weight of iron having a surface area greater than about 50 $m^2/g$, about 0.1 to about 5 parts-by-weight of platinum, about 2 wt. % to about 20 wt. % nickel per 100 parts-by-weight of a silica support.

20. A catalyst for the conversion of carbon dioxide into syngas, wherein the catalyst is an impregnated, metal-coated spinel comprising about 2 to about 25 parts-by-weight of iron having a surface area greater than about 50 $m^2/g$, about 0.1 to about 5 parts-by-weight of rhenium, about 2 wt. % to about 20 wt. % nickel per 100 parts-by-weight of a silica support.

21. A catalyst for the conversion of carbon dioxide into syngas, wherein the catalyst is an impregnated, metal-coated spinel comprising about 2 to about 25 parts-by-weight of magnesium having a surface area greater than about 50 $m^2/g$, about 0.1 to about 5 parts-by-weight of cerium, about 2 wt. % to about 20 wt. % nickel per 100 parts-by-weight of an alumina support.

22. A catalyst for the conversion of carbon dioxide into syngas, wherein the catalyst is an impregnated, metal-coated spinel comprising about 2 to about 25 parts-by-weight of magnesium having a surface area greater than about 50 $m^2/g$, about 0.1 to about 5 parts-by-weight of ruthenium, about 2 wt. % to about 20 wt. % nickel per 100 parts-by-weight of an alumina support.

23. A catalyst for the conversion of carbon dioxide into syngas, wherein the catalyst is an impregnated, metal-coated spinel comprising about 2 to about 25 parts-by-weight of magnesium having a surface area greater than about 50 $m^2/g$, about 0.1 to about 5 parts-by-weight of lanthanum, about 2 wt. % to about 20 wt. % nickel per 100 parts-by-weight of an alumina support.

24. A catalyst for the conversion of carbon dioxide into syngas, wherein the catalyst is an impregnated, metal-coated spinel comprising about 2 to about 25 parts-by-weight of magnesium having a surface area greater than about 50 $m^2/g$, about 0.1 to about 5 parts-by-weight of platinum, about 2 wt. % to about 20 wt. % nickel per 100 parts-by-weight of an alumina support.

25. A catalyst for the conversion of carbon dioxide into syngas, wherein the catalyst is an impregnated, metal-coated spinel comprising about 2 to about 25 parts-by-weight of magnesium having a surface area greater than about 50 $m^2/g$, about 0.1 to about 5 parts-by-weight of rhenium, about 2 wt. % to about 20 wt. % nickel per 100 parts-by-weight of an alumina support.

26. A catalyst for the conversion of carbon dioxide into syngas, wherein the catalyst is an impregnated, metal-coated spinel comprising about 2 to about 25 parts-by-weight of magnesium having a surface area greater than about 50 $m^2/g$, about 0.1 to about 5 parts-by-weight of cerium, about 2 wt. % to about 20 wt. % nickel per 100 parts-by-weight of a silica support.

27. A catalyst for the conversion of carbon dioxide into syngas, wherein the catalyst is an impregnated, metal-coated spinel comprising about 2 to about 25 parts-by-weight of magnesium having a surface area greater than about 50 $m^2/g$, about 0.1 to about 5 parts-by-weight of ruthenium, about 2 wt. % to about 20 wt. % nickel per 100 parts-by-weight of a silica support.

28. A catalyst for the conversion of carbon dioxide into syngas, wherein the catalyst is an impregnated, metal-coated spinel comprising about 2 to about 25 parts-by-weight of magnesium having a surface area greater than about 50 $m^2/g$, about 0.1 to about 5 parts-by-weight of lanthanum, about 2 wt. % to about 20 wt. % nickel per 100 parts-by-weight of a silica support.

29. A catalyst for the conversion of carbon dioxide into syngas, wherein the catalyst is an impregnated, metal-coated spinel comprising about 2 to about 25 parts-by-weight of magnesium having a surface area greater than about 50 $m^2/g$, about 0.1 to about 5 parts-by-weight of platinum, about 2 wt. % to about 20 wt. % nickel per 100 parts-by-weight of a silica support.

30. A catalyst for the conversion of carbon dioxide into syngas, wherein the catalyst is an impregnated, metal-coated spinel comprising about 2 to about 25 parts-by-weight of magnesium having a surface area greater than about 50 $m^2/g$, about 0.1 to about 5 parts-by-weight of rhenium, about 2 wt. % to about 20 wt. % nickel per 100 parts-by-weight of a silica support.

31. A catalyst for the conversion of carbon dioxide into syngas, wherein the catalyst is an impregnated, metal-coated spinel comprising about 2 to about 25 parts-by-weight of manganese having a surface area greater than about 50 $m^2/g$, about 0.1 to about 5 parts-by-weight of cerium, about 2 wt. % to about 20 wt. % nickel per 100 parts-by-weight of an alumina support.

32. A catalyst for the conversion of carbon dioxide into syngas, wherein the catalyst is an impregnated, metal-coated spinel comprising about 2 to about 25 parts-by-weight of manganese having a surface area greater than about 50 $m^2/g$, about 0.1 to about 5 parts-by-weight of ruthenium, about 2 wt. % to about 20 wt. % nickel per 100 parts-by-weight of an alumina support.

33. A catalyst for the conversion of carbon dioxide into syngas, wherein the catalyst is an impregnated, metal-coated spinel comprising about 2 to about 25 parts-by-weight of manganese having a surface area greater than about 50 $m^2/g$, about 0.1 to about 5 parts-by-weight of lanthanum, about 2 wt. % to about 20 wt. % nickel per 100 parts-by-weight of an alumina support.

34. A catalyst for the conversion of carbon dioxide into syngas, wherein the catalyst is an impregnated, metal-coated spinel comprising about 2 to about 25 parts-by-weight of manganese having a surface area greater than about 50 $m^2/g$, about 0.1 to about 5 parts-by-weight of platinum, about 2 wt. % to about 20 wt. % nickel per 100 parts-by-weight of an alumina support.

35. A catalyst for the conversion of carbon dioxide into syngas, wherein the catalyst is an impregnated, metal-coated spinel comprising about 2 to about 25 parts-by-weight of manganese having a surface area greater than about 50 $m^2/g$, about 0.1 to about 5 parts-by-weight of rhenium, about 2 wt. % to about 20 wt. % nickel per 100 parts-by-weight of an alumina support.

36. A catalyst for the conversion of carbon dioxide into syngas, wherein the catalyst is an impregnated, metal-coated spinel comprising about 2 to about 25 parts-by-weight of manganese having a surface area greater than about 50 $m^2/g$, about 0.1 to about 5 parts-by-weight of cerium, about 2 wt. % to about 20 wt. % nickel per 100 parts-by-weight of a silica support.

37. A catalyst for the conversion of carbon dioxide into syngas, wherein the catalyst is an impregnated, metal-coated spinel comprising about 2 to about 25 parts-by-weight of manganese having a surface area greater than about 50 $m^2/g$, about 0.1 to about 5 parts-by-weight of ruthenium, about 2 wt. % to about 20 wt. % nickel per 100 parts-by-weight of a silica support.

38. A catalyst for the conversion of carbon dioxide into syngas, wherein the catalyst is an impregnated, metal-coated spinel comprising about 2 to about 25 parts-by-weight of manganese having a surface area greater than about 50 $m^2/g$, about 0.1 to about 5 parts-by-weight of lanthanum, about 2 wt. % to about 20 wt. % nickel per 100 parts-by-weight of a silica support.

39. A catalyst for the conversion of carbon dioxide into syngas, wherein the catalyst is an impregnated, metal-coated spinel comprising about 2 to about 25 parts-by-weight of manganese having a surface area greater than about 50 $m^2/g$, about 0.1 to about 5 parts-by-weight of platinum, about 2 wt. % to about 20 wt. % nickel per 100 parts-by-weight of a silica support.

40. A catalyst for the conversion of carbon dioxide into syngas, wherein the catalyst is an impregnated, metal-coated spinel comprising about 2 to about 25 parts-by-weight of manganese having a surface area greater than about 50 $m^2/g$, about 0.1 to about 5 parts-by-weight of rhenium, about 2 wt. % to about 20 wt. % nickel per 100 parts-by-weight of a silica support.

41. A catalyst for the conversion of carbon dioxide into syngas, wherein the catalyst is an impregnated, metal-coated spinel comprising about 2 to about 25 parts-by-weight of calcium having a surface area greater than about 50 $m^2/g$, about 0.1 to about 5 parts-by-weight of cerium, about 2 wt. % to about 20 wt. % nickel per 100 parts-by-weight of an alumina support.

42. A catalyst for the conversion of carbon dioxide into syngas, wherein the catalyst is an impregnated, metal-coated spinel comprising about 2 to about 25 parts-by-weight of calcium having a surface area greater than about 50 $m^2/g$, about 0.1 to about 5 parts-by-weight of ruthenium, about 2 wt. % to about 20 wt. % nickel per 100 parts-by-weight of an alumina support.

43. A catalyst for the conversion of carbon dioxide into syngas, wherein the catalyst is an impregnated, metal-coated spinel comprising about 2 to about 25 parts-by-weight of calcium having a surface area greater than about 50 $m^2/g$, about 0.1 to about 5 parts-by-weight of lanthanum, about 2 wt. % to about 20 wt. % nickel per 100 parts-by-weight of an alumina support.

44. A catalyst for the conversion of carbon dioxide into syngas, wherein the catalyst is an impregnated, metal-coated spinel comprising about 2 to about 25 parts-by-weight of calcium having a surface area greater than about 50 $m^2/g$, about 0.1 to about 5 parts-by-weight of platinum, about 2 wt. % to about 20 wt. % nickel per 100 parts-by-weight of an alumina support.

45. A catalyst for the conversion of carbon dioxide into syngas, wherein the catalyst is an impregnated, metal-coated spinel comprising about 2 to about 25 parts-by-weight of calcium having a surface area greater than about 50 $m^2/g$, about 0.1 to about 5 parts-by-weight of rhenium, about 2 wt. % to about 20 wt. % nickel per 100 parts-by-weight of an alumina support.

46. A catalyst for the conversion of carbon dioxide into syngas, wherein the catalyst is an impregnated, metal-coated spinel comprising about 2 to about 25 parts-by-weight of calcium having a surface area greater than about 50 $m^2/g$, about 0.1 to about 5 parts-by-weight of cerium, about 2 wt. % to about 20 wt. % nickel per 100 parts-by-weight of a silica support.

47. A catalyst for the conversion of carbon dioxide into syngas, wherein the catalyst is an impregnated, metal-coated spinel comprising about 2 to about 25 parts-by-weight of calcium having a surface area greater than about 50 $m^2/g$, about 0.1 to about 5 parts-by-weight of ruthenium, about 2 wt. % to about 20 wt. % nickel per 100 parts-by-weight of a silica support.

48. A catalyst for the conversion of carbon dioxide into syngas, wherein the catalyst is an impregnated, metal-coated spinel comprising about 2 to about 25 parts-by-weight of calcium having a surface area greater than about 50 $m^2/g$, about 0.1 to about 5 parts-by-weight of lanthanum, about 2 wt. % to about 20 wt. % nickel per 100 parts-by-weight of a silica support.

49. A catalyst for the conversion of carbon dioxide into syngas, wherein the catalyst is an impregnated, metal-coated spinel comprising about 2 to about 25 parts-by-weight of calcium having a surface area greater than about 50 $m^2/g$, about 0.1 to about 5 parts-by-weight of platinum, about 2 wt. % to about 20 wt. % nickel per 100 parts-by-weight of a silica support.

50. A catalyst for the conversion of carbon dioxide into syngas, wherein the catalyst is an impregnated, metal-coated spinel comprising about 2 to about 25 parts-by-weight of calcium having a surface area greater than about 50 $m^2/g$, about 0.1 to about 5 parts-by-weight of rhenium, about 2 wt. % to about 20 wt. % nickel per 100 parts-by-weight of a silica support.

51. A catalyst for the conversion of carbon dioxide into syngas, wherein the catalyst is an impregnated, metal-coated spinel comprising about 2 to about 25 parts-by-weight of barium having a surface area greater than about 50 $m^2/g$, about 0.1 to about 5 parts-by-weight of cerium, about 2 wt. % to about 20 wt. % nickel per 100 parts-by-weight of an alumina support.

52. A catalyst for the conversion of carbon dioxide into syngas, wherein the catalyst is an impregnated, metal-coated spinel comprising about 2 to about 25 parts-by-weight of barium having a surface area greater than about 50 $m^2/g$, about 0.1 to about 5 parts-by-weight of ruthenium, about 2 wt. % to about 20 wt. % nickel per 100 parts-by-weight of an alumina support.

53. A catalyst for the conversion of carbon dioxide into syngas, wherein the catalyst is an impregnated, metal-coated spinel comprising about 2 to about 25 parts-by-weight of barium having a surface area greater than about 50 $m^2/g$, about 0.1 to about 5 parts-by-weight of lanthanum, about 2 wt. % to about 20 wt. % nickel per 100 parts-by-weight of an alumina support.

54. A catalyst for the conversion of carbon dioxide into syngas, wherein the catalyst is an impregnated, metal-coated spinel comprising about 2 to about 25 parts-by-weight of barium having a surface area greater than about 50 $m^2/g$, about 0.1 to about 5 parts-by-weight of platinum, about 2 wt. % to about 20 wt. % nickel per 100 parts-by-weight of an alumina support.

55. A catalyst for the conversion of carbon dioxide into syngas, wherein the catalyst is an impregnated, metal-coated spinel comprising about 2 to about 25 parts-by-weight of barium having a surface area greater than about 50 $m^2/g$, about 0.1 to about 5 parts-by-weight of rhenium, about 2 wt. % to about 20 wt. % nickel per 100 parts-by-weight of an alumina support.

56. A catalyst for the conversion of carbon dioxide into syngas, wherein the catalyst is an impregnated, metal-coated spinel comprising about 2 to about 25 parts-by-weight of barium having a surface area greater than about 50 $m^2/g$, about 0.1 to about 5 parts-by-weight of cerium, about 2 wt. % to about 20 wt. % nickel per 100 parts-by-weight of a silica support.

57. A catalyst for the conversion of carbon dioxide into syngas, wherein the catalyst is an impregnated, metal-coated spinel comprising about 2 to about 25 parts-by-weight of barium having a surface area greater than about 50 $m^2/g$, about 0.1 to about 5 parts-by-weight of ruthenium, about 2 wt. % to about 20 wt. % nickel per 100 parts-by-weight of a silica support.

58. A catalyst for the conversion of carbon dioxide into syngas, wherein the catalyst is an impregnated, metal-coated spinel comprising about 2 to about 25 parts-by-weight of barium having a surface area greater than about 50 $m^2/g$, about 0.1 to about 5 parts-by-weight of lanthanum, about 2 wt. % to about 20 wt. % nickel per 100 parts-by-weight of a silica support.

59. A catalyst for the conversion of carbon dioxide into syngas, wherein the catalyst is an impregnated, metal-coated spinel comprising about 2 to about 25 parts-by-weight of barium having a surface area greater than about 50 $m^2/g$, about 0.1 to about 5 parts-by-weight of platinum, about 2 wt. % to about 20 wt. % nickel per 100 parts-by-weight of a silica support.

60. A catalyst for the conversion of carbon dioxide into syngas, wherein the catalyst is an impregnated, metal-coated spinel comprising about 2 to about 25 parts-by-weight of barium having a surface area greater than about 50 $m^2/g$, about 0.1 to about 5 parts-by-weight of rhenium, about 2 wt. % to about 20 wt. % nickel per 100 parts-by-weight of a silica support.

61. A catalyst for the conversion of carbon dioxide into syngas, wherein the catalyst is an impregnated, metal-coated spinel comprising about 2 to about 25 parts-by-weight of copper having a surface area greater than about 50 $m^2/g$, about 0.1 to about 5 parts-by-weight of cerium, about 2 wt. % to about 20 wt. % nickel per 100 parts-by-weight of an alumina support.

62. A catalyst for the conversion of carbon dioxide into syngas, wherein the catalyst is an impregnated, metal-coated spinel comprising about 2 to about 25 parts-by-weight of copper having a surface area greater than about 50 $m^2/g$, about 0.1 to about 5 parts-by-weight of ruthenium, about 2 wt. % to about 20 wt. % nickel per 100 parts-by-weight of an alumina support.

63. A catalyst for the conversion of carbon dioxide into syngas, wherein the catalyst is an impregnated, metal-coated spinel comprising about 2 to about 25 parts-by-weight of copper having a surface area greater than about 50 $m^2/g$, about 0.1 to about 5 parts-by-weight of lanthanum, about 2 wt. % to about 20 wt. % nickel per 100 parts-by-weight of an alumina support.

64. A catalyst for the conversion of carbon dioxide into syngas, wherein the catalyst is an impregnated, metal-coated spinel comprising about 2 to about 25 parts-by-weight of copper having a surface area greater than about 50 $m^2/g$, about 0.1 to about 5 parts-by-weight of platinum, about 2 wt. % to about 20 wt. % nickel per 100 parts-by-weight of an alumina support.

65. A catalyst for the conversion of carbon dioxide into syngas, wherein the catalyst is an impregnated, metal-coated spinel comprising about 2 to about 25 parts-by-weight of copper having a surface area greater than about 50 $m^2/g$, about 0.1 to about 5 parts-by-weight of rhenium, about 2 wt. % to about 20 wt. % nickel per 100 parts-by-weight of an alumina support.

66. A catalyst for the conversion of carbon dioxide into syngas, wherein the catalyst is an impregnated, metal-coated spinel comprising about 2 to about 25 parts-by-weight of copper having a surface area greater than about 50 $m^2/g$, about 0.1 to about 5 parts-by-weight of cerium, about 2 wt. % to about 20 wt. % nickel per 100 parts-by-weight of a silica support.

67. A catalyst for the conversion of carbon dioxide into syngas, wherein the catalyst is an impregnated, metal-coated spinel comprising about 2 to about 25 parts-by-weight of copper having a surface area greater than about 50 $m^2/g$, about 0.1 to about 5 parts-by-weight of ruthenium, about 2 wt. % to about 20 wt. % nickel per 100 parts-by-weight of a silica support.

68. A catalyst for the conversion of carbon dioxide into syngas, wherein the catalyst is an impregnated, metal-coated spinel comprising about 2 to about 25 parts-by-weight of copper having a surface area greater than about 50 $m^2/g$, about 0.1 to about 5 parts-by-weight of lanthanum, about 2 wt. % to about 20 wt. % nickel per 100 parts-by-weight of a silica support.

69. A catalyst for the conversion of carbon dioxide into syngas, wherein the catalyst is an impregnated, metal-coated spinel comprising about 2 to about 25 parts-by-weight of copper having a surface area greater than about 50 $m^2/g$, about 0.1 to about 5 parts-by-weight of platinum, about 2 wt. % to about 20 wt. % nickel per 100 parts-by-weight of a silica support.

70. A catalyst for the conversion of carbon dioxide into syngas, wherein the catalyst is an impregnated, metal-coated spinel comprising about 2 to about 25 parts-by-weight of copper having a surface area greater than about 50 m²/g, about 0.1 to about 5 parts-by-weight of rhenium, about 2 wt. % to about 20 wt. % nickel per 100 parts-by-weight of a silica support.

71. A catalyst for the conversion of carbon dioxide into syngas, wherein the catalyst is an impregnated, metal-coated spinel comprising about 2 to about 25 parts-by-weight of zinc having a surface area greater than about 50 m²/g, about 0.1 to about 5 parts-by-weight of cerium, about 2 wt. % to about 20 wt. % nickel per 100 parts-by-weight of an alumina support.

72. A catalyst for the conversion of carbon dioxide into syngas, wherein the catalyst is an impregnated, metal-coated spinel comprising about 2 to about 25 parts-by-weight of zinc having a surface area greater than about 50 m²/g, about 0.1 to about 5 parts-by-weight of ruthenium, about 2 wt. % to about 20 wt. % nickel per 100 parts-by-weight of an alumina support.

73. A catalyst for the conversion of carbon dioxide into syngas, wherein the catalyst is an impregnated, metal-coated spinel comprising about 2 to about 25 parts-by-weight of zinc having a surface area greater than about 50 m²/g, about 0.1 to about 5 parts-by-weight of lanthanum, about 2 wt. % to about 20 wt. % nickel per 100 parts-by-weight of an alumina support.

74. A catalyst for the conversion of carbon dioxide into syngas, wherein the catalyst is an impregnated, metal-coated spinel comprising about 2 to about 25 parts-by-weight of zinc having a surface area greater than about 50 m²/g, about 0.1 to about 5 parts-by-weight of platinum, about 2 wt. % to about 20 wt. % nickel per 100 parts-by-weight of an alumina support.

75. A catalyst for the conversion of carbon dioxide into syngas, wherein the catalyst is an impregnated, metal-coated spinel comprising about 2 to about 25 parts-by-weight of zinc having a surface area greater than about 50 m²/g, about 0.1 to about 5 parts-by-weight of rhenium, about 2 wt. % to about 20 wt. % nickel per 100 parts-by-weight of an alumina support.

76. A catalyst for the conversion of carbon dioxide into syngas, wherein the catalyst is an impregnated, metal-coated spinel comprising about 2 to about 25 parts-by-weight of zinc having a surface area greater than about 50 m²/g, about 0.1 to about 5 parts-by-weight of cerium, about 2 wt. % to about 20 wt. % nickel per 100 parts-by-weight of a silica support.

77. A catalyst for the conversion of carbon dioxide into syngas, wherein the catalyst is an impregnated, metal-coated spinel comprising about 2 to about 25 parts-by-weight of zinc having a surface area greater than about 50 m²/g, about 0.1 to about 5 parts-by-weight of ruthenium, about 2 wt. % to about 20 wt. % nickel per 100 parts-by-weight of a silica support.

78. A catalyst for the conversion of carbon dioxide into syngas, wherein the catalyst is an impregnated, metal-coated spinel comprising about 2 to about 25 parts-by-weight of zinc having a surface area greater than about 50 m²/g, about 0.1 to about 5 parts-by-weight of lanthanum, about 2 wt. % to about 20 wt. % nickel per 100 parts-by-weight of a silica support.

79. A catalyst for the conversion of carbon dioxide into syngas, wherein the catalyst is an impregnated, metal-coated spinel comprising about 2 to about 25 parts-by-weight of zinc having a surface area greater than about 50 m²/g, about 0.1 to about 5 parts-by-weight of platinum, about 2 wt. % to about 20 wt. % nickel per 100 parts-by-weight of a silica support.

80. A catalyst for the conversion of carbon dioxide into syngas, wherein the catalyst is an impregnated, metal-coated spinel comprising about 2 to about 25 parts-by-weight of zinc having a surface area greater than about 50 m²/g, about 0.1 to about 5 parts-by-weight of rhenium, about 2 wt. % to about 20 wt. % nickel per 100 parts-by-weight of a silica support.

Reactors

1. A catalytic conversion system for the conversion of carbon dioxide into a liquid fuel, wherein the catalytic system comprises a first catalytic reactor and a second catalytic reactor, wherein the first catalytic reactor comprises a first catalyst, wherein the first catalyst that is a Nickel and Magnesium solid-solution catalyst, ideally the catalyst includes $Ni_2Mg$, wherein the second catalytic reactor comprises a second catalyst, wherein the second catalyst comprises about 2 to about 25 parts-by-weight cobalt and from about 0.1 to about 5 parts-by-weight of at least one metal selected from a group consisting of cerium, ruthenium, lanthanum, platinum, or rhenium per 100 parts-by-weight of a support selected from a group consisting of silica, alumina, and combinations thereof.

2. The catalytic conversion system according to reactor 1 above, wherein the catalytic conversion system further comprises a heat exchanger between the first catalytic reactor and the second catalytic reactor, wherein gas flows from the first catalytic reactor to the heat exchanger and then to the second catalytic reactor.

3. The catalytic conversion system according to reactor 1 above, wherein the catalytic conversion system further comprises a gas blending chamber that is connected to the first catalytic reactor such that gas can flow between the gas blending chamber to the first catalytic reactor.

4. The catalytic conversion system according to reactor 1 above, wherein the catalytic conversion system further comprises an electrolysis system for the production of hydrogen, wherein the electrolysis system is connected to the gas blending chamber such that hydrogen produced in the electrolysis system can flow to the gas blending chamber.

5. The catalytic conversion system according to reactor 3 above, wherein the catalytic conversion system further comprises a system for capturing carbon dioxide, wherein the system for capturing carbon dioxide is connected to the gas blending chamber such that carbon dioxide obtained in the carbon dioxide capturing system can flow to the gas blending system.

6. The catalytic conversion system according to reactor 4 above, wherein the catalytic conversion system further comprises a system for capturing carbon dioxide, wherein the system for capturing carbon dioxide is connected to the gas blending chamber such that carbon dioxide obtained in the carbon dioxide capturing system can flow to the gas blending system.

Integrated Conversion System

1. A process for the production of a liquid fuel, wherein the process comprises the steps of: a) separating oxygen from ambient air using a cryogenic air separator; b) mixing the oxygen with natural gas in the presence of heated supercritical carbon dioxide at high pressure and high temperature, thereby combusting the natural gas, producing combustion gases comprising carbon dioxide and water, along with heat; c) passing the combustion gases through a gas turbine generator, thereby generating electricity that is used for at least two purposes, and wherein the at least two purposes are distribution to the electric grid and use in the process for production of the liquid fuel and allowing the combustion gases to exit the gas turbine generator; d) further passing the combustion gases through a heat exchanger, wherein the heat exchanger reduces the temperature of the combustion gases; e) removing water from the combustion gases to provide carbon dioxide; f) introducing a portion of the carbon dioxide along with hydrogen, or a mixture of the carbon dioxide portion with hydrogen and light hydrocarbons, into a first catalytic reactor in a catalytic conversion system to produce syngas, wherein the first catalyst that is a Nickel and Magnesium solid-solution catalyst, ideally the catalyst includes $Ni_2Mg$, and compressing any remaining carbon dioxide while heating it to provide supercritical carbon dioxide; g) introducing the syngas into a second catalytic reactor in the catalytic conversion system to produce tailgas, water and liquid fuel, wherein the second catalyst comprises about 2 to about 25 parts-by-weight of an element wherein the element is selected from a group of elements consisting of cobalt, iron, magnesium, manganese, calcium, barium, copper and zinc, and from about 0.1 to about 5 parts-by-weight of at least one metal selected from a group consisting of cerium, ruthenium, lanthanum, platinum, or rhenium per 100 parts-by-weight of a support selected from a group consisting of silica, alumina, and combinations thereof, thereby producing liquid fuel, tailgas and water; h) separating the liquid fuel, tailgas and water from one another thereby producing the liquid fuel.

Production Plant

1. A liquid fuel production plant, wherein the plant can produce at least 400 barrels per day of drop-in, synthetic liquid fuel while producing very little carbon dioxide emissions and using less than 80 MW of power, wherein the plant comprises: a) a cryogenic air separator that separates oxygen from ambient air, wherein the cryogenic air separator is connected to a combustions system that uses the oxygen to combust natural gas, producing carbon dioxide and water; b) a gas turbine power generator that is connected to the combustion system, allowing combustion products including gaseous carbon dioxide and water to flow through the gas turbine power generator, producing electricity; c) a heat exchanger connected to the gas turbine power generator, such that gaseous carbon dioxide and water exiting the gas turbine is introduced to the heat exchanger, which cools the gaseous carbon dioxide and water; d) a cooler and mist separator connected to the heat exchanger such that cooled gas from the heat exchanger flows into the cooler and mist separator, thereby removing water from the gas stream and producing carbon dioxide; e) a first catalytic reactor connected to the cooler and mist separator such that the carbon dioxide is introduced into the first catalytic reactor, wherein the first catalyst that is a Nickel and Magnesium solid-solution catalyst, ideally the catalyst includes $Ni_2Mg$, and the first catalytic reactor is capable of producing syngas; f) a second catalytic reactor connected to the first catalytic reactor such that syngas flows from the first catalytic reactor to the second catalytic reactor, wherein the second catalytic reactor comprises a second catalyst, wherein the second catalyst comprises about 2 to about 25 parts-by-weight cobalt and from about 0.1 to about 5 parts-by-weight of at least one metal selected from a group consisting of cerium, ruthenium, lanthanum, platinum, or rhenium per 100 parts-by-weight of a support selected from a group consisting of silica, alumina, and combinations thereof and the second catalytic reactor is capable of producing liquid fuel from syngas.

Further Processes and Catalysts

1. A process that efficiently converts $CO_2/H_2$ mixtures, or mixtures of $CO_2/H_2$ and light hydrocarbons, directly into synthetic liquid fuels by employing a catalytic process which contains two catalysts in which the first is an improved, high-surface area solid solution catalyst for the production of syngas, and the second is an improved structured catalyst that directly converts the syngas into synthetic fuels.

2. The process according to further processes and catalysts 1 above in which $H_2$ is produced from water using electrolysis.

3. The process according to further processes and catalysts 1 above in which $H_2$ may be produced from the steam reforming of solid carbonaceous substances such as biomass, flare gas, biogas, methane, light hydrocarbons and other constituents that contain various stoichiometric mixtures of carbon, hydrogen and oxygen.

4. The process according to further processes and catalysts 1 above in which the $CO_2$ may be captured from traditional power plants, oxy-combustion power plants, fermentation processes, cement plants, ambient air $CO_2$ capture systems, biogas, waste-water treatment plants, secondary oil recovery, refineries, chemical production plants, geothermal power plants, nylon plants, or ammonia plants.

5. The process according to further processes and catalysts 1 above in which the ratios of the $H_2/CO_2$ mixture input into the catalytic conversion process may vary from 1.5/1.0 to 5.0/1.0, and preferably 2.0/1.0 to 3.0/1.0.

6. The process according to further processes and catalysts 1 above in which the $H_2/CO_2$ mixture is input into the catalytic converter at pressures between 25 and 400 psi.

7. The process according to further processes and catalysts 1 above in which the $H_2/CO_2$ mixture is input into the catalytic converter at pressures between 150 and 325 psi.

8. The process according to further processes and catalysts 1 above in which the $H_2/CO_2$ mixture is heated to a temperature that is greater than the operating temperature of the first catalyst so that the first catalyst requires little or no additional heating.

9. The process according to further processes and catalysts 1 above in which the first and second catalysts in the catalytic reactor operate at nearly the same pressure.

10. The process according to further processes and catalysts 1 above in which the first catalyst is an improved solid solution catalyst consisting primarily of 2-35 wt. % $Ni_2Mg$ supported on a high surface area alumina spinel which may be comprised of a Co-alumina spinel, an Fe-alumina spinel, a Mg-alumina spinel, a Mn-alumina spinel, a Ca-alumina spinel, a Ba-alumina spinel, a Ni-alumina spinel, a Cu-alumina spinel or a Zn-alumina spinel, and in which M is a metal such as Mg, Mn, Ca, Ba, Cu, Zn or Sr.

11. The improved solid-solution catalyst according to further processes and catalysts 9 above in which the first catalyst may contain 0.1 to about 5.0 parts-by-weight of promoters which consist of at least one or more transition or rare-earth metals per 100 parts-by-weight of the support.

12. The improved solid-solution catalyst according further processes and catalysts 9 above in which the catalyst contains less than 0.05% rare metals.

13. The improved solid-solution catalyst according to further processes and catalysts 9 above in which water soluble salts of nickel and the promoters are impregnated on the spinel substrate, dried and calcined at temperatures up to 2,100° F.

14. The calcined catalyst according to further processes and catalysts 12 above which is primarily comprised of 5-35 wt. % of $Ni_2MgO_2$ and 0.2-5.0 wt. % of the oxides of the promoters.

15. The calcined catalyst according to further processes and catalysts 13 above which may be used in tubular fixed bed reactors, fluidized bed reactors, moving bed reactors, rotating bed reactors, slurry bed reactors and other reactors commonly used in the art.

16. The calcined catalyst according to further processes and catalysts 13 above, which is reduced at temperatures up to about 1,200° F. with $H_2$ or other reducing agents typically employed in the art to form primarily $Ni_2Mg$ and the elemental forms of the one or more transition or rare-earth metals.

17. The reduced catalyst according to further processes and catalysts 15 above which efficiently converts mixtures of $H_2$ and $CO_2$ to syngas when the catalyst is operated at pressures in the range of 20-200 psi and more preferably in the range of 50-150 psi.

18. The catalyst according to further processes and catalysts 15 above which efficiently converts mixtures of $H_2$ and $CO_2$ to syngas when the catalyst is operated at 5,000 to 200,000 $hr^1$ space velocity.

19. The catalyst according to further processes and catalysts 15 above which efficiency converts mixtures of $H_2$ and $CO_2$ to syngas in which the $H_2$ to $CO_2$ ratio may vary from 1.0 to 4.0, preferably from 1.5 to 3.5, and more preferably from 2.0 to 3.0.

20. The catalyst according to further processes and catalysts 15 above in which syngas is produced with a $CO_2$ to CO conversion efficiency of greater than about 55% at 1,600° F. at 50-300 psi pressures.

21. The catalyst according to further processes and catalysts 15 above which produces syngas with an $H_2/CO$ ratio in the range of 1.0-3.0 and preferably 1.5-2.5.

22. The catalyst according to further processes and catalysts 15 above which has a thermal stability up to 2,100° F.

23. The catalyst according to further processes and catalysts 15 above which is resistant to contaminants present in captured $CO_2$ streams, natural gas, biogas or other gas feedstock streams.

24. The catalyst according to further processes and catalysts 15 above in which the catalyst forms no or nominal carbon via coking.

25. The catalyst according to further processes and catalysts 15 above in which $CH_4$, when present in the $CO_2/H_2$ mixture, is efficiently converted to syngas.

26. The catalyst according to further processes and catalysts 15 above in which $C_2$-$C_7$ hydrocarbons, when present in the $CO_2/H_2$ mixture, are efficiently converted to syngas.

27. The process according to further processes and catalysts 15 above which efficiently produces syngas when $O_2$ is added to the selected mixtures of $CO_2$, $H_2$, $CH_4$, and $C_2$-$C_5$ hydrocarbons.

28. The process according to further processes and catalysts 15 above in which the syngas is feed into other catalytic reactors to produce fuels and/or chemicals.

29. The process according to further processes and catalysts 15 above in which a heat exchanger is used to reduce the temperature from the first catalyst to the operating temperature of the second catalyst to 400-475° F.

30. The process according to further processes and catalysts 28 above in which the cooled syngas is feed into a second catalyst, and wherein this second catalyst comprises from about 2 to about 50 parts-by-weight cobalt and from about 0.1 to about 10 parts-by-weight of at least one metal selected from a group consisting of cerium, ruthenium, lanthanum, platinum, palladium, and rhenium per 100 parts-by-weight of a support selected from a group consisting of silica, alumina, and combinations thereof, thereby producing a diesel fuel.

31. The process according to further processes and catalysts 29 above in which the second catalyst produces $C_1$-$C_5$ gas-phase hydrocarbons; $C_5$-$C_{23}$ liquid phase hydrocarbons; a tail-gas consisting of CO, $H_2$, $C_1$-$C_5$ hydrocarbons, $CO_2$; $H_2O$; and $C_{24}+$ hydrocarbons.

32. The process according to further processes and catalysts 30 above, comprising introducing the product stream from the second reactor system into a separator that separates the $C_{24}+$ hydrocarbons from the other products.

33. The process according to further processes and catalysts 30 above in which the partitioning of the $C_{24}+$ hydrocarbons from the $C_5$-$C_{23}$ hydrocarbons is controlled by varying the separator temperature.

34. The process according to further processes and catalysts 31 above in which the remaining liquid product stream is condensed into two fractions wherein the top fraction contains the liquid hydrocarbon fuel and the bottom fraction comprises water.

35. The process according to further processes and catalysts 33 above in which the liquid hydrocarbon fuel is separated from the water.

36. The process of further processes and catalysts 34 above in which the liquid hydrocarbon fuel is used directly for off-road diesel engines and vehicles.

37. The process of further processes and catalysts 34 above in which the liquid hydrocarbon fuel is blended with petroleum diesel fuel and used for on-road diesel engines and vehicles.

38. The process of further processes and catalysts 34 above in which the synthetic liquid fuel is distilled to produce diesel fuel #1; diesel fuel #2; jet fuel; reformulated gasoline blendstocks; and a minor fraction (less than about 5 volume %) of heavy ($C_{24}+$) hydrocarbons.

39. The process of further processes and catalysts 37 above in which the reformulated gasoline blendstock is blended with petroleum gasoline fuels and used for spark-ignition engines and vehicles.

40. The process of further processes and catalysts 37 above in which the diesel #1 (kerosene) is used for kerosene heaters and stoves.

41. The process of further processes and catalysts 37 above in which the diesel #1 (kerosene) is used for jet engines and turbines.

42. The process of further processes and catalysts 37 above in which the neat or blended synthetic fuels reduce criteria engine emissions by at least 2% compared to petroleum based fuels.

43. The process of further processes and catalysts 37 above in which the neat or blended synthetic fuels improve one or more fuel properties by at least 2% compared to petroleum based fuels.

44. The process of further processes and catalysts 37 above in which the neat or blended synthetic fuels reduce greenhouse gas emissions by at least 2% compared to petroleum based fuels.

45. The process according to further processes and catalysts 34 above in which some of the tailgas is recycled back to catalyst #2 for the production of additional products.

46. The process according to further processes and catalysts 34 above in which some of the tailgas is converted to additional syngas by partial oxidation with oxygen (e.g. ATR conversion) or by autothermal reforming (ATR) produced from electrolysis.

47. The process according to further processes and catalysts 45 above in which the heated syngas is added to the $H_2/CO_2$ stream before input into the first catalyst.

48. The process according to further processes and catalysts 1-28 above in which the syngas is feed into other types of catalytic processes to produce fuels and/or chemicals.

49. The process of further processes and catalysts 47 above in which the second catalyst is a Fischer Tropsch type catalyst formulation that produces wax, followed by the conversion of that wax into fuels and/or chemicals using conventional wax hydro-reforming and hydro-processing methods.

50. The process of further processes and catalysts 47 above in which the second catalyst produces methanol, ethanol and/or other alcohols.

51. The process of further processes and catalysts 47 above in which the second catalyst is used for the production of methanol, the methanol which is then converted into gasoline using additional, conventional catalysts and processes described in the current art.

52. The process according to further processes and catalysts 47 above in which the syngas is used to produce power using gen-sets, gas-turbines and other established gas to power equipment.

53. The process according to any one of further processes and catalysts 47 above in which the syngas is used as a burner fuel for the production of heat.

54. The process of further processes and catalysts 47 above in which the second catalyst is used for the production of ammonia.

Example

This illustrative example describes the conversion of $CO_2$ from an oxy-fuel combustion power plant to liquid fuels. As described earlier, the direct production of liquid fuels from $CO_2$ utilizing these improved catalysts and processes can use the $CO_2$ obtained from, but not limited to traditional power plants, oxy-combustion power plants, ethanol fuel production plants, cement plants, ambient air $CO_2$ capture systems, geothermal power plants, and other $CO_2$ emission sources.

The primary difference between these sources is the cost of obtaining relatively pure $CO_2$ and the cost of the power used to generate H2 by water electrolysis. Since oxy-combustion power plants have the potential of directly producing CO2 at little or no cost and supplying power at a reasonable cost for $H_2$ production, the direct conversion of liquid fuels produced from $CO_2$ is the key example described herein.

Oxy-fuel combustion is the process of combusting a hydrocarbon fuel in a nearly pure oxygen environment, as opposed to air. Although coal has been tested in oxy-fuel combustion plants, the combustion of coal produces high quantities of particulates (fly-ash) and sulfur oxides (e.g. SO, $SO_2$ and $SO_3$). Therefore, the preferred hydrocarbon fuel is natural gas.

One of the most promising oxy-fuel combustion processes utilizes the Allam cycle (Allam et al, 2017). This system uses a semi-closed-loop, high-pressure, low-pressure-ratio recuperated Brayton cycle that uses supercritical $CO_2$ as the working fluid which dramatically reduces energy losses compared to steam- and air-based cycles. In conventional cycles, the separation and removal of low concentration combustion derived impurities such as $CO_2$ results in a large additional capital cost and increased parasitic power increasing the cost of electricity by 50% to 70%. The compelling economics of the Allam Cycle are driven by high target efficiencies, 59% net for natural gas (LHV basis) while capturing nearly 100% $CO_2$ at pipeline pressure with low projected capital and O&M costs. Additionally, for a small reduction in performance the cycle can run substantially water free. The system employs only a single turbine, utilizes a small plant footprint, and requires smaller and fewer components than conventional hydrocarbon fueled systems.

FIG. 5 illustrates the primary processes for the Allam oxy-fuel combustion process and integration of the direct liquid fuel production process with an Allam Oxy-Fuel Combustion Process. A cryogenic air separator 501 is used to separate oxygen 503 from ambient air 502. The oxygen 503 is mixed with natural gas 504 in the presence of heated supercritical carbon dioxide at high pressure (~320 bar) and high temperature (~720° C.) 20.

The combustion produces additional carbon dioxide, water, and lots of heat 506. Some CO may be produced, depending upon the oxygen to natural gas ratio, combustion pressure and temperature, and power loads under gas-turbine conditions (Wang and Stiegel, 2017). However CO formation is very low when the combustion system is operated at or very near stoichiometric conditions ($O_2$/fuel=1.00).

The hot, high-pressure mixture is then passed through a gas turbine generator 507, where the high-pressure gas stream rotates a shaft to generate electricity. Most of the power is distributed to the grid 508 and the remainder is used for the direct liquid fuel production process 510. The pressure of the gas stream 511 exiting the gas turbine is reduced to about 30 bars at about 720° C.

The gas stream 511 is passed through a heat exchanger 512 which reduces its temperature to 43° C. while maintaining the 30 bar pressure. A cooler 513 and a mist separator 514 removes water 515 from the $CO_2$ stream. The water contains a small amount of sulfates which are derived from the combustion of the sulfur in the natural gas. The sulfates, other particulates and dissolved contaminants in the water are removed by the direct liquid fuel production process 510.

Some of the $CO_2$ 516 is used by the direct liquid fuel production plant and the remainder of the $CO_2$ 517 is compressed 518 and heated 512 to about 320 bars and 720° C. These conditions create supercritical $CO_2$ 519. Any excess $CO_2$ 520 can be used for other purposes such as the production of dry ice.

As a result, this process produces no emissions. The heat transfer in this process is so efficient that for each unit of energy trapped in natural gas; this cycle produces 0.8 units of electricity (compared to 0.6 units produced by the most advanced natural-gas power plants).

This example describes the innovative process for the direct liquid fuel production from $CO_2$, which employs the innovative catalytic converter and process, integrated with a 300 MW Allam cycle oxy-combustion plant.

The direct liquid fuel production plant is designed to produce about 450 barrels/day of drop-in, synthetic liquid fuels from 91,000 metric tons/year of $CO_2$, 78.06 MW of power and condensed water generated by the oxy-combustion plant.

| U.S. Patent Application Documents | | |
|---|---|---|
| 2003/0113244 A1 | June 2003 | DuPont et al |
| 2005/0166447 A1 | August 2005 | Corkwell et al |

-continued

| U.S. Patent Application Documents | | |
|---|---|---|
| 2006/0144755 A1 | July 2006 | Benazzi et al |
| 2008/0108716 A1 | May 2008 | Ayasse |
| 2009/0300970 A1 | December 2009 | Perego et al |
| 2010/0160463 A1 | June 2010 | Wang et al |
| 2012/0208902 A1 | August 2012 | Kresnyak et al |
| 2017/0321333 A1 | November 2017 | Kuhl et al |

| U.S. Patent Documents | | |
|---|---|---|
| 4,990,491 A | June 1988 | Wagner et al |
| 6,402,989 B1 | June 2002 | Gaffney et al |
| 6,423,665 B1 | July 2002 | Okado et al |
| 6,946,114 B2 | September 2005 | Allison et al |
| 7,432,222 B2 | October 2008 | Choudhary et al |
| 7,718,832 B1 | May 2010 | Schuetzle et al |
| 8,198,338 B1 | xx/2012 | Schulenberger et al |
| 8,394,862 B1 | March 2013 | Schuetzle et al |
| 8,741,001 B1 | June 2014 | Schuetzle et al |
| 9,090,831 B2 | July 2015 | Schuetzle et al |
| 9,095,813 B2 | September 2015 | Keith et al |
| 9,476,002 B1 | October 2016 | Schuetzle et al |
| 9,611,145 B1 | April 2017 | Schuetzle et al |
| 9,631,147 B1 | April 2017 | Schuetzle et al |
| 10,478,806 B1 | November 2019 | Schuetzle et al |

| Foreign Patent Documents | | |
|---|---|---|
| AU 2015/203898 B2 | July 2015 | Landau et al |
| GB 1995/2279583 A | November 1995 | Iwanani et al |

OTHER PUBLICATIONS

Allam, R., Palmer, M. R., Brown, W., Fetvedta, J., Freeda, D., Nomoto, H., Itoh, M., Okita, N., Jones, C.: High efficiency and low cost of electricity generation from fossil fuels while eliminating atmospheric emissions, including carbon dioxide, Energy Procedia 37, 1135-1149 (2013) (DOI: 10.1016/j.egypro.2017.03.1731).

Allam, R., Martin, S., Forrest, B., Fetvedt, J., Lu, X., Freed, D., Brown, W., Sasaki, T., Itoh, M., Manning, J.: Demonstration of the Allam cycle: an update on the development status of a high efficiency supercritical carbon dioxide power process employing full carbon capture, Energy Procedia 114, 5949-5966 (2017) (DOI: 10.1016/j.egypro.2017.03.1731).

Arakawa, H.: Catalysis research of relevance to carbon management: progress, challenges, and opportunities. Chem. Rev. 101, 953-996 (2001) (DOI: 10.1021/cr000018s).

Artz, J., Müller, T. E., Thenert, K., Kleinekorte, J., Meys, R., Sternberg, A., Bardow, A, Leitner, W: Sustainable conversion of carbon dioxide: An integrated review of catalysis and life cycle assessment. Chemical Reviews, 118, 434-504 (2018).

Ashcroft, A. T., Cheetham, A. K., Green, M. L. H., and Vernon, P. D. F.: Partial oxidation of methane to synthesis gas using carbon dioxide, Nature, 352, 255-256 (1991).

Bahmanpour, A. M., Heroguel, F., Kilic, M., Baranowski, C. J., Artiglia, L.: Cu—Al spinel as a highly active catalyst for the reverse water gas shift reaction. ACS Catal., 9, 6243-6251 (2019).

Centi, G., Perathoner, S.: Opportunities and prospects in the chemical recycling of carbon dioxide to fuels. Catalysis Today 148, 191-205 (2009) (DOI: 10.1016/j.cattod.2009.07.075).

Chen, P., Zhao, Guofeng, Z., Xue-Rong, J., Zhu, J. D., Lu, Y.: Catalytic technology for carbon dioxide reforming of methane to syngas. iScience 17, 315-324 (2019) (DOI: 10.1016/j.isci.2019.07.006).

Choudhary, V. R., Dajput, A. M., and Brabhapar, B.: Energy efficient methane-to-syngas conversion with low $H_2/CO$ ratio by simultaneous catalytic reactions of methane, Catalysis Letters, 32, 391-396 (1995).

Daza, Y. A., Kuhn, J. N.: $CO_2$ conversion by reverse water gas shift catalysis: Comparison of catalysts, mechanisms and their consequences for $CO_2$ conversion to liquid fuels, Royal Society of Chemistry Advances, 1-31 (2016) (DOI: 10.1039/C6RA05414E).

Fischer, N., Claeys, M., Van Steen, E., Niemantsverdriet, H., Vosloo, M.: Syngas convention—fuels and chemicals from synthesis gas: state of the art 2, 1-200 (2016).

Fulkerson, W., Judkins, R. R., Sanghvi, M. K.: Energy from fossil fuels, Scientific American, 263, 128-135 (1990) (DOI: 10.1038/scientificamerican0990-128).

Hill, M. R.: How to make renewable natural gas, 2018, 2018 AGA-EPA RNG Workshop (Oct. 23, 2018).

Intergovernmental Panel on Climate Change: IPCC special report on $CO_2$ capture and storage, Cambridge University Press, Cambridge (2005).

Jafari, M., Sadaf, A., Behroozarand, A., Ghasemzadeh, K., Wood, D. A.: Plant-wide simulation of an integrated zero-emission process to convert flare gas to gasoline, Gas Processing Journal, 6, 1-20 (2018) (DOI: 10.22108/gpj.2018.111048.1028).

Jiang, Z., Xiao, T., Kuznetsov, V. L., Edwards, P. P.: Turning carbon dioxide into fuel. Phil. Trans. R. Soc. A, 368, 3343-3364 (2010) (DOI: 10.1098/rsta.2010.0119).

Kothandaraman, J., Goeppert, A., Czaun, M., Olah, G. A., Prakash, G. K. S.: Conversion of $CO_2$ from air into methanol using a polyamine and a homogeneous ruthenium catalyst J. Am. Chem. Soc. 138, 778-781 (2016) (DOI:10.1021/jacs.5b12354).

Li, W., Wang, H., Jiang, X., Zhu, J., Liu, Z., Guo, X., Song, C.: A short review of recent advances in $CO_2$ hydrogenation to hydrocarbons over heterogeneous catalysts, RSC Adv., 8, 7651 (2018) (DOI: 10.1039/c7ra13546g).

Lortie, M.: Reverse water gas shift reaction over supported Cu—Ni nanoparticle catalysts, Department of Chemical and Biological Engineering M.S. Thesis, University of Ottawa, Ottawa, Canada (2014).

Marti, C., Pacifici, L., Capriccioli, A., Lagana, A.: Simulation of methane production from carbon dioxide on a collaborative research infrastructure, International Conference on Computational Science and Its Applications ICCSA 2016: Computational Science and Its Applications—ICCSA, 319-333 (2016).

Melaina, M. W., Antonia, O., Penev, M.: Blending hydrogen into natural gas pipeline networks: a review of key issues. National Renewable Energy Laboratory, Technical Report #5600-51995 (2013).

Messias, S., Sousa, M. M., daPonte, M. N., Rangel, C. M., Pardal, T., Machado, A. S. R.: Electro-chemical production of syngas from $CO_2$ at pressures up to 30 bars in electrolytes containing ionic liquid, React. Chem. Eng., 4, 1982-1990 (2019).

Metz, B., Davidson, O., de Connick, H. C., Loos, M., Meyer, L. A.: IPCC special report on carbon dioxide capture and storage, Intergovernmental Panel on Climate Change, Cambridge University Press, Cambridge, United Kingdom and New York, N.Y., USA, 442 pages (2005).

Mikkelsen, M., Jorgensen, M., Krebs, F. C.: The teraton challenge—a review of fixation and transformation of carbon dioxide. *Energy Environ. Sci.* 3, 43-81 (2010) (DOI: 10.1039/b912904a).

National Academy of Sciences, Chemical Utilization of $CO_2$ into Chemicals and Fuels, Gaseous Carbon Waste Streams Utilization: Status and Research Needs, National Academies Press, Washington D.C. (2019) (DOI: 10.17226/25232).

Olah, G. A.: Beyond oil and gas: the methanol economy. Angew. Chem. Int. Edn. 44, 2636-2639 (2005) (DOI: 10.1002/anie.200462121).

Olah, G. A., Goeppert, A., Surya Prakash, G. K.: Chemical recycling of carbon dioxide to methanol and dimethyl ether—from greenhouse gas to renewable, environmentally carbon neutral fuels and synthetic hydrocarbons. J. Org. Chem. 74, 487-498 (2009) (DOI: 10.1021/jo801260f).

Owen, R. E., Mattia, D., Plucinski, P., Jones, M. D., Kinetics of $CO_2$ hydrogenation to hydrocarbons over Iron-Silica catalysts, Physical Chemistry, 18, 3211-3218 (2017).

Pan, X., Fan, Z., Chen, W., Ding, Y., Luo, H. & Bao, X.: Enhanced ethanol production inside carbon-nanotube reactors containing catalytic particles, Nat. Mater. 6, 507-511 (2007) (DOI: 10.1038/nmat1916).

Pearson, R. J., Turner, J. W. G., Peck, A. J.: Gasoline-ethanol-methanol tri-fuel vehicle development and its role in expediting sustainable organic fuels for transport. *Low carbon vehicles*, Institute of Mechanical Engineers Conference, London, May 2009 (2009) (www.grouplotus.com/mediagallery/image/1002548.pdf).

Ruckenstein, E., Hu, Y. H.: Combination of $CO_2$ reforming and partial oxidation of methane over NiO/MgO Solid Solution, Industrial & Engineering Chemistry Research, 37, 1744-1747 (1998).

Sakakura, T., Choi, J.-C., Yasuda, H.: Transformation of carbon dioxide. Chem. Rev. 107, 2365-2387 (2007) (DOI: 10.1021/cr068357u).

Senderens, J.-B., Sabatier, P.: Nouvelles syntheses du méthane. Comptes Rendus Acad. Sci. 82, 514-516 (1902).

Safriet, D.: Emission factor documentation for AP-12, Section 9.12.2 Wines and Brandy, U.S. EPA, Office of Air Quality Planning and Standards, Research Triangle Park, N.C. (October 1995).

Semelsberger, T. A., Borup, R. L., Greene, H. L.: Dimethyl Ether (DME) as an alternative fuel, Journal of Power Sources 156, 497-511 (2006).

SoCalGas, Renewable natural gas (RNG) gas quality standards (www.socalgas.com/rg) (2019).

Schuetzle, D., Tamblyn, G., Caldwell, M., Schuetzle, R.: Solar reforming of carbon dioxide to produce diesel fuel. DOE report #DE-FE0002558 (2010).

Schuetzle, D.: Historical and predicted global climate changes and some potential accelerated climate moderation approaches, 2018 Global Climate Action Summit, San Francisco, Calif., 1-42 (Sep. 10-14, 2018); Research Gate (www.researchgate.net) (Apr. 24, 2017 and Jan. 26, 2020 update).

Vogt, C., Monai, M., Kramer, G. J., Weckhuysen, B. M.: The renaissance of the Sabatier reaction and its applications on Earth and in space, Nature Catalysis, 2, 188-197 (2019).

Wang, W., Wang, S., Ma, X, Gong, J.: Recent advances in catalytic hydrogenation of carbon dioxide, Chem. Soc. Rev, 40, 3703-3727 (2011) (DOI: 10.1039/c1cs15008a).

Wang, Y., Liu, T., Lei, L., Chen, F.: High temperature solid oxide $H_2O/CO_2$ co-electrolysis for syngas production, Fuel Processing Technology, 161 (2016) (10.1016/j.fuproc.2016.08.009).

Wang, T., Stiegel, G.: Integrated gasification combined cycle (IGCC) technologies, Elsevier, Oxford, U.K. (2017).

Williamson, D., Herdes, C., Torrente-Murciano, L., Jones, M., Mattia, D.: N-doped Fe for combined RWGS-FT $CO_2$ hydrogenation, 7, 7395-7402, ACS Sustainable Chem. Engineering (2019).

Wieclaw-Solny, L., Tararczuk, A., Krótki, A., Stec, M.: The technological research progress of amine-based CO2 capture, Polityka Energ. 16, 229-240 (2013).

Wikipedia: Energy density (2013) (www.en.wikipedia.org/wiki-/Energy_density).

Zaki, T., Sakr, A., Natural gas origin, composition and processing: a review, Journal of Natural Gas Science and Engineering 34 (2016); DOI: 10.1016/j.jngse.2016.06.030.

Zhang, J., Wang, H., and Dalai, A. K., Development of stable bimetallic catalysts for carbon dioxide reforming of methane. Journal of Catalysis, 249, 300-310 (2007).

Zhou, Z., Ersoy, D.: Review studies of hydrogen use in natural gas distribution systems, Gas Technology Institute, Chicago, Ill., National Renewable Energy Laboratory, Technical Report #21029 (2010).

Zhu, Q.: Developments on $CO_2$-utilization technologies, Clean Energy, 3, 85-100 (2019) (DOI: 10.1093/ce/zkz008).

What is claimed is:

1. A process for the conversion of carbon dioxide into a liquid fuel, wherein the process comprises the steps of:
   a) Producing hydrogen and oxygen from the electrolysis of water;
   b) Introducing the hydrogen in combination with carbon dioxide into a first catalytic reactor that uses a first catalyst wherein the output from the first catalytic reactor is syngas and wherein the first catalyst is a transition metal solid-solution catalyst, and wherein the first solid solution catalyst includes $Ni_2Mg$;
   c) Introducing the syngas into a second catalytic reactor that uses a second catalyst to produce tailgas, water and liquid fuel;
   d) Introducing the tailgas from the second catalytic reactor to a tailgas conversion system that utilizes oxygen from the electrolyzer to produce additional syngas.

2. The process according to claim 1, wherein the transition metal in the first solid solution catalyst is Nickel.

3. The process according to claim 1, wherein the tailgas conversion system is partial oxidation.

4. The process according to claim 1, wherein the tailgas conversion system is autothermal reforming.

5. The process according to claim 1, wherein the first catalytic reactor and the second catalytic reactor operate at pressures that are within 50 psi of each other.

6. The process according to claim 1, wherein the syngas is introduced into a heat exchanger to reduce the temperature of the syngas before it is introduced into the second catalytic reactor.

7. The process according to claim 1, wherein the carbon dioxide introduced into the first catalytic reactor is obtained from a source, wherein the source is selected from a group of sources consisting of oxy-combustion power plants, ambient air $CO_2$ capture systems, natural gas well-heads, ethanol production facilities, chemical production facilities and secondary oil recovery processes.

8. The process according to claim 1, wherein the hydrogen is generated using electrolysis, wherein the power for the electrolysis is generated from a renewable or low-carbon source, and wherein the renewable or low carbon source is selected from a group of sources consisting of wind, solar, geothermal, hydro, ocean currents, biomass, flare gas, nuclear, off-peak power from a fossil fuel plant, and power produced by an oxy-combustion plant.

9. The process according to claim 1, wherein the second catalytic reactor is operated at a pressure from about 50 psi to about 300 psi, from about 50 psi to about 250 psi, from about 50 psi to about 200 psi, from about 50 psi to about 150 psi, or from about 50 psi to about 100 psi.

10. The process according to claim 1, wherein the first catalyst is an impregnated, metal-coated spinel comprising about 2 to about 25 parts-by-weight of magnesium having a surface area greater than about 50 $m^2/g$, wherein the first catalyst further comprises about 2 wt. % to about 20 wt. % nickel.

11. A process for the production of a liquid fuel, wherein the process comprises the steps of:
  a) Separating oxygen from ambient air using a cryogenic air separator;
  b) Mixing the oxygen with natural gas in the presence of heated supercritical carbon dioxide at high pressure and high temperature, thereby combusting the natural gas, producing combustion gases comprising carbon dioxide and water, along with heat;
  c) Passing the combustion gases through a gas turbine generator, thereby generating electricity that is used for at least two purposes, and wherein the at least two purposes are distribution to the electric grid and use in the process for production of the liquid fuel and allowing the combustion gases to exit the gas turbine generator;
  d) Further passing the combustion gases through a heat exchanger, wherein the heat exchanger reduces the temperature of the combustion gases;
  e) Removing water from the combustion gases to provide carbon dioxide;
  f) Introducing a portion of the carbon dioxide along with hydrogen, or a mixture of the carbon dioxide portion with hydrogen and light hydrocarbons, into a first catalytic reactor in a catalytic conversion system to produce syngas, wherein the first catalyst is a $Ni_2Mg$ solid-solution catalyst, and compressing any remaining carbon dioxide while heating it to provide supercritical carbon dioxide;
  g) Introducing the syngas into a second catalytic reactor in the catalytic conversion system to produce tailgas, water and liquid fuel, wherein the second catalyst comprises about 2 to about 25 parts-by-weight of an element wherein the element is selected from a group of elements consisting of cobalt, iron, magnesium, manganese, calcium, barium, copper and zinc, and from about 0.1 to about 5 parts-by-weight of at least one metal selected from a group consisting of cerium, ruthenium, lanthanum, platinum, or rhenium per 100 parts-by-weight of a support selected from a group consisting of silica, alumina, and combinations thereof, thereby producing liquid fuel, tailgas and water;
  h) Separating the liquid fuel, tailgas and water from one another thereby producing the liquid fuel.

* * * * *